United States Patent
Feucht et al.

(10) Patent No.: US 6,734,139 B1
(45) Date of Patent: May 11, 2004

(54) N-ARYL-URACILE-BASED HERBICIDES

(75) Inventors: Dieter Feucht, Monheim (DE); Peter Dahmen, Neuss (DE); Mark Wilhelm Drewes, Langenfeld (DE); Birgit Krauskopf, Leawood, KS (US); Mathias Kremer, Burscheid (DE); Rolf Pontzen, Leichlingen (DE); Ingo Wetcholowsky, Estancia Marambaia (BR); Roland Andree, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/148,771

(22) PCT Filed: Nov. 21, 2000

(86) PCT No.: PCT/EP00/11833

§ 371 (c)(1),
(2), (4) Date: Aug. 28, 2002

(87) PCT Pub. No.: WO01/39597

PCT Pub. Date: Jun. 7, 2001

(30) Foreign Application Priority Data

Dec. 3, 1999 (DE) .......................... 199 58 381

(51) Int. Cl.⁷ ...................... C67D 239/55; A01N 43/54; A01N 43/80

(52) U.S. Cl. .................. 504/128; 504/243; 504/136; 544/309; 544/310; 544/311; 544/312; 544/313; 544/314

(58) Field of Search ................ 504/243, 128, 504/136; 544/309, 310, 311, 312, 313, 314

(56) References Cited

U.S. PATENT DOCUMENTS

| 4,943,309 A | 7/1990 | Bell | 71/74 |
|---|---|---|---|
| 5,084,084 A | 1/1992 | Satow et al. | 71/92 |
| 5,127,935 A | 7/1992 | Satow et al. | 71/92 |
| 5,154,755 A | 10/1992 | Satow et al. | 71/92 |
| 5,183,492 A | 2/1993 | Suchy et al. | 504/243 |
| 5,356,863 A | 10/1994 | Satow et al. | 504/243 |
| 5,593,945 A | 1/1997 | Andree et al. | 504/243 |
| 5,681,794 A | 10/1997 | Friese | 504/243 |
| 5,759,957 A | 6/1998 | Andree et al. | 504/243 |
| 6,077,813 A | 6/2000 | Linker et al. | 504/272 |
| 6,110,870 A | 8/2000 | Andree et al. | 504/243 |
| 6,175,010 B1 | 1/2001 | Andree et al. | 544/310 |
| 6,331,507 B1 | 12/2001 | Linker et al. | 504/244 |
| 6,420,316 B1 | 7/2002 | Linker et al. | 504/273 |
| 6,451,736 B1 | 9/2002 | Linker et al. | 504/210 |
| 6,511,940 B1 | 1/2003 | Ziemer et al. | 504/118 |
| 2002/0004457 A1 | 1/2002 | Nevill et al. | 504/138 |

FOREIGN PATENT DOCUMENTS

| CA | 2199846 | 3/1996 |
|---|---|---|
| DE | 35 25 371 | 7/1986 |
| DE | 195 00 439 | 11/1995 |
| DE | 44 312 19 | 3/1996 |
| DE | 44 37 197 | 4/1996 |
| DE | 195 06 202 | 8/1996 |
| DE | 195 16 785 | 11/1996 |
| DE | 195 47 475 | 1/1997 |
| DE | 199 19 951 | 9/1999 |
| EP | 047 35 51 | 3/1992 |
| EP | 07 14 602 | 6/1996 |
| WO | 97/34484 | 9/1997 |
| WO | 99/11130 | 3/1999 |

OTHER PUBLICATIONS

Chemical Patents Index, Documentation Abstracts Journal, Section Ch, Week 199938, Oct. 15, 1999 Derwent Publications Ltd., London, GB; Class C02, AN 1999–452880 XP002170145 & JP 11 189506 A (Nissan Chem Ind Ltd), Jul. 13, 1999 cited in the application abstract.

Weeds, (month unavailable) 1967, pp. 20–22, "Calculating Synergistic and Antagonistic Responses of Herbicide Combinations" by S. R. Colby.

*Primary Examiner*—Sabiha Qazi
(74) *Attorney, Agent, or Firm*—Richard E.L. Henderson; Raymond J. Harmuth

(57) ABSTRACT

The present invention provides herbicidal active compound combinations which comprise, N-aryl-uracils and herbicidally active compounds and/or compounds which improve crop plant compatibility. The combinations find use in controlling monocotyledonous and dicotyledonous weeds in crops of useful plants.

6 Claims, No Drawings

N-ARYL-URACILE-BASED HERBICIDES

FIELD OF THE INVENTION

The invention relates to novel herbicidal active compound combinations comprising, on the one hand, known N-aryluracils and, on the other hand, known herbicidally active compounds and/or compounds which improve crop plant compatibility, which combinations can be used with particularly good results for controlling monocotyledonous and dicotyledonous weeds in various crops of useful plants, but also for controlling monocotyledonous and dicotyledonous weeds in the semi- and non-selective field.

BACKGROUND OF THE INVENTION

N-aryl-uracils are, as herbicidally active compounds, subject of a number of patent applications (cf. EP-A-408382, EP-A-473551, EP-A-563384, EP-A-648749, U.S. Pat. No. 4,943,309, U.S. Pat. No. 5,084,084, U.S. Pat. No. 5,127,935, U.S. Pat. No. 5,759,957, WO-A-91/00278, WO-A-95/29168, WO-A-95/30661, WO-A-96/35679, WO-A-97/01541, WO-A-98/25909). However, the known N-aryluracils have a number of gaps in their activity.

A number of herbicidally active compound combinations based on N-aryl-uracils have also been disclosed (cf. DE-A-4437197, DE-A-19915013, DE-A-19919951, EP-A-714602, WO-A-96/07323, WO-A-96/08151, JP-A-11189506). However, likewise, the properties of these active compound combinations are not entirely satisfactory.

DETAILED DESCRIPTION OF THE INVENTION

Surprisingly, it has now been found that a number of known active compounds from the group of the N-aryluracils, when used together with known herbicidally active compounds, show synergistic effects with respect to the activity against weeds and can be used particularly advantageously as broadly active combination preparations for the selective control of monocotyledonous and dicotyledonous weeds in crops of useful plants, such as, for example, cotton, cereals, grass/pasture land, maize, lawn ("turf"), rice, soyabeans, sunflowers and sugar cane, but also for controlling monocotyledonous and dicotyledonous weeds in the semi- and non-selective field.

The present invention provides herbicidal compositions, characterized in that they comprise an effective amount of an active compound combination comprising (a) at least one N-aryl-uracil of the formula (I)

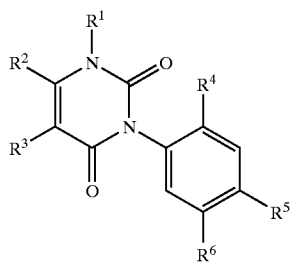

(I)

in which
R$^1$ represents hydrogen, amino or optionally cyano-, halogen- or C$_1$–C$_4$-alkoxy-substituted alkyl having 1 to 5 carbon atoms,
R$^2$ represents optionally halogen-substituted alkyl having 1 to 5 carbon atoms,
R$^3$ represents hydrogen, halogen or optionally halogen-substituted alkyl having 1 to 5 carbon atoms,
R$^4$ represents hydrogen, cyano or halogen,
R$^5$ represents cyano, thiocarbamoyl or halogen, and
R$^6$ represents nitro, cyano, carboxyl, carbamoyl, thiocarbamoyl, hydroxyl, mercapto, amino, hydroxyamino, aminosulphonyl, halogen, represents in each case optionally cyano-, hydroxyl-, C$_1$–C$_4$-alkoxy-, C$_1$–C$_4$-alkyl-carbonyl-, C$_1$–C$_4$-alkoxy-carbonyl-, C$_2$–C$_4$-alkenyloxy-carbonyl-, C$_2$–C$_4$-alkinyloxy-carbonyl-, C$_1$–C$_4$-alkylamino-carbonyl-, di-(C$_1$–C$_4$-alkyl)-amino-carbonyl-, phenoxycarbonyl- and/or phenylaminocarbonyl-substituted alkyl, alkoxy, alkylthio, alkylsulphinyl, alkylsulphonyl, alkylcarbonyl, alkoxycarbonyl or alkylamino having in each case up to 6 carbon atoms, represents in each case optionally cyano-, carboxyl-, halogen- and/or C$_1$–C$_4$-alkoxy-carbonyl-substituted alkenyl, alkinyl, alkenyloxy or alkinyloxy having in each case up to 6 carbon atoms, represents in each case optionally halogen- or C$_1$–C$_4$-alkoxy-substituted alkylcarbonylamino, alkoxycarbonylamino, alkylsulphonylamino, N,N-bis-alkylsulphonyl-amino or N-alkylcarbonyl-N-alkylsulphonyl-amino having in each case up to 6 carbon atoms in the alkyl groups, or represents phenyloxy, naphthyloxy, N-phenylcarbonyl-N-alkylsulphonyl-amino, N-pyridylcarbonyl-N-alkylsulphonyl-amino, N-furylcarbonyl-N-alkylsulphonyl-amino or N-thienylcarbonyl-N-alkylsulphonyl-amino having in each case up to 6 carbon atoms in the alkyl groups and being in each case optionally substituted by cyano or halogen, or by C$_1$–C$_4$-alkyl, C$_1$–C$_4$-alkoxy or C$_1$–C$_4$-alkoxy-carbonyl (which are in each case optionally substituted by C$_1$–C$_4$-alkoxy-carbonyl, C$_3$–C$_4$-alkenyloxy-carbonyl or C$_3$–C$_4$-alkinyloxy-carbonyl), ("Active Compounds of Group 1")
and
(b) at least one compound from a second group of herbicides comprising the active compounds listed below:
2-chloro-N-(ethoxymethyl)-N-(2-ethyl-6-methyl-phenyl)-acetamide (acetochlor), 5-(2-chloro-4-trifluoromethyl-phenoxy)-2-nitro-benzoic acid sodium salt (acifluorfen-sodium), 2-chloro-6-nitro-3-phenoxy-benzenamine (aclonifen), 2-chloro-N-(methoxymethyl)-N-(2,6-diethyl-phenyl)-acetamide (alachlor), N-ethyl-N'-i-propyl-6-methylthio-1,3,5-triazine-2,4-diamine (ametryn), 4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methylsulphonyl-sulphamoyl)-urea (amidosulfuron), 1H-1,2,4-triazol-3-amine (amitrole), 6-chloro-4-ethylamino-2-isopropylamino-1,3,5-triazine (atrazine), 2-[2,4-dichloro-5-(2-propinyloxy)-phenyl]-5,6,7,8-tetrahydro-1,2,4-triazolo-[4,3-a]-pyridin-3(2H)-one (azafenidin), N-(4,6-dimethoxy-pyrimidin-2-yl)-N'-[1-methyl-4-(2-methyl-2H-tetrazol-5-yl)-1H-pyrazol-5-ylsulphonyl]-urea (azimsulfuron), N-benzyl-2-(4-fluoro-3-trifluoromethyl-phenoxy)-butanamide (beflubutamid), 4-chloro-2-oxo-3(2H)- benzothiazoleacetic acid (benazolin), N-butyl-N-ethyl-2,6-dinitro-4-trifluoromethyl-benzenamine (benfluralin), N-(4,6-dimethoxy-pyrimidin-2-yl)-N'-(2-methoxycarbonyl-phenylmethylsulphonyl)-urea (bensulfuron), methyl 2-[2-[4-(3,6-dihydro-3-methyl-2,6-dioxo-4-trifluoromethyl-1(2H)-pyrimidinyl)phenoxy]methyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), ethyl N-benzoyl-N-(3,4-dichloro-phenyl)-DL-alaninate (benzoylprop-ethyl), 3-i-propyl-1H-2,1,3-benzothiadiazin-4(3H)-one (bentazone), methyl 5-(2,4-dichloro-phenoxy)-2-nitro-benzoate (bifenox), 2,6-bis-(4,6-dimethoxy-pyrimidin-2-yl-oxy)-benzoic acid sodium salt (bispyribac-sodium), 5-bromo-6-methyl-3-(1-methyl-propyl)-2,4(1H,3H) pyrimidinedione (bromacil), 2-bromo-3,3-dimethyl-N-(1-methyl-1-phenyl-ethyl)-butanamide (bromobutide), O-(2,4-dinitro-phenyl) 3,5-dibromo-4-hydroxy-benzaldehyde-oxime (bromofenoxim), 3,5-dibromo-4-hydroxy-benzonitrile (bromoxynil), N-butoxymethyl-2-chloro-N-(2,6-diethyl-phenyl)-acetamide (butachlor), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), S-ethyl bis-(2-methyl-propyl)-thiocarbamate (butylate), N,N-diethyl-3-(2,4,6-trimethyl-phenylsulphonyl)-1H-1,2,4-triazole-1-carboxamide (cafenstrole), 2-[1-[(3-chloro-2-propenyl)-oxyimino]-propyl]-3-hydroxy-5-(tetrahydro-2H-pyran-4-yl)-2-cyclohexen-1-one (caloxydim, tepraloxydim), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), 2,4-dichloro-1-(3-methoxy-4-nitro-phenoxy)-benzene (chlomethoxyfen), 3-amino-2,5-dichloro-benzoic acid (chloramben), N-(4-chloro-6-methoxy-pyrimidin-2-yl)-N'-(2-ethoxycarbonyl-phenylsulphonyl)-urea (chlorimuron-ethyl), 1,3,5-trichloro-2-(4-nitro-phenoxy)-benzene (chlomitrofen), N-(4-methoxy-6-methyl-1,3,5-triazin-2-yl)-N'-(2-chloro-phenylsulphonyl)-urea (chlorsulfuron), N'-(3-chloro-4-methyl-phenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidonethyl), N-(4,6-dimethoxy-1,3,5-triazin-2-yl)-N'-(2-(2-methoxy-ethoxy)-phenylsulphonyl)-urea (cinosulfuron), 2-[1-[2-(4-chloro-phenoxy)-propoxyamino]butyl]-5-(tetrahydro-2H-thiopyran-3-yl)-1,3-cyclohexanedione (clefoxydim), (E,E)-(+)-2-[1-[[(3-chloro-2-propenyl)-oxy]-imino]-propyl]-3-hydroxy-2-cyclohexen-1-one (clethodim), prop-2-inyl (R)-2-[4-(5-chloro-3-fluoro-pyridin-2-yl-oxy)-phenoxy]-propanoate (clodinafop-propargyl), 3,6-dichloro-pyridine-2-carboxylic acid (clopyralid), methyl 3-chloro-2-[(5-ethoxy-7-fluoro[1,2,4] triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), 2,4-dichloro-phenoxyacetic acid (2,4-D), 3,6-dichloro-2-methoxy-benzoic acid (dicamba), (R)-2-(2,4-dichloro-phenoxy)-propanoic acid (dichlorprop-P), methyl-2-[4-(2,4-dichloro-phenoxy)-phenoxy]-propanoate (diclofop-methyl), N-(2,6-dichloro-phenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methylsulphate (difenzoquat), N-(2,4-difluoro-phenyl)-2-(3-trifluoromethyl-phenoxy)-pyridine-3-carboxamide (diflufenican), 2-[1-[(3,5-difluoro-phenyl)-amino-carbonyl-hydrazono]-ethyl]-pyridine-3-carboxylic acid (diflufenzopyr), S-(1-methyl-1-phenyl-ethyl) 1-piperidine-carbothioate (dimepiperate), 2-chloro-N-(2,6-dimethyl-phenyl)-N-(2-methoxy-ethyl)-acetamide (dimethachlor), (S-) 2-chloro-N-(2,4-dimethyl-3-thienyl)-N-(2-methoxy-1-methyl-ethyl)-acetamide (S-) (dimethenamid), 2-amino-4-(1-fluoro-1-methyl-ethyl)-6-(1-methyl-2-(3,5-dimethyl-phenoxy)-ethylamino)-1,3,5-triazine (dimexyflam), N3,N3-diethyl-2,4-dinitro-6-trifluoromethyl-1,3-diamino-benzene (dinitramine), 6,7-dihydro-dipyrido[1,2-a:2',1'-c]pyrazinediium (diquat), S,S-dimethyl 2-difluoromethyl-4-i-butyl-6-trifluoromethyl-pyridine-3,5-dicarbothioate (dithiopyr), N'-(3,4-dichloro-phenyl)-N,N-dimethyl-urea (diuron), 2-[2-(3-chloro-phenyl)-oxiranylmethyl]-2-ethyl-1H-indene-1,3(2H)-dione (epropodan), S-ethyl dipropylthiocarbamate (EPTC), S-(phenylmethyl) N-ethyl-N-(1,2-dimethyl-propyl)-thiocarbamate (esprocarb), N-ethyl-N-(2-methyl-2-propenyl)-2,6-dinitro-4-trifluoromethyl-benzenamine (ethalfluralin), 2-ethoxy-1-methyl-2-oxoethyl (S)-2-chloro-5-(2-chloro-4-trifluoromethyl-phenoxy)-benzoate (ethoxyfen), N-(4,6-dimethoxy-pyrimidin-2-yl)-N'-(2-ethoxy-phenoxysulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamid), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluorobenzoate (fluazolate), 4,5-dihydro-3-methoxy-4-methyl-5-oxo-N-[(2-trifluoromethoxy-phenyl)-sulphonyl]-1H-1,2,4-triazole-1-carboxamide sodium salt (flucarbazone-sodium), N-(4-fluoro-phenyl)-N-i-propyl-2-(5-trifluoromethyl-1,3,4-thiadiazol-2-yl-oxy)-acetamide (flufenacet), N-(2,6-difluoro-phenyl)-5-methyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H- isoindol-2-yl)-phenoxy]-acetate (flumiclorac-pentyl), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propinyl)-oxy]-phenyl]-4,5,6,7-tetrahydro-1H-isoindole-1,3(2H)-dione (flumipropyn), 3-chloro-4-chloromethyl-1-(3-trifluoromethyl-phenyl)-2-pyrrolidinone (fluorochloridone), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-fluorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxypropyl, -meptyl), 5-methylamino-2-phenyl-4-(3-trifluoromethyl-phenyl)-3(2H)-furanone (flurtamone), methyl [(2-chloro-4-fluoro-5-(tetrahydro-3-oxo-1H,3H-[1,3,4]-thiadiazolo-[3,4-a]-pyridazin-1-yliden)-amino)-phenyl]-thio-acetate (fluthiacet-methyl), 5-(2-chloro-4-trifluoromethyl-phenoxy)-N-methylsulphonyl-2-nitro-benzamide (fomesafen), 2-[[[[(4,6-dimethoxy-2-pyrimidinyl)-amino]-carbonyl]-amino]-sulphonyl]-4-formylamino-N,N-dimethyl-benzamide (foramsulfuron), 2-amino-4-(hydroxymethylphosphinyl)-butanoic acid (ammonium salt) (glufosinate-(ammonium)), N-phosphonomethyl-glycine (isopropylammonium salt) (glyphosate, isopropylammonium), (R)-2-[4-(3-chloro-5-trifluoromethyl-pyridin-2-yl-oxy)-phenoxy]-propanoic acid (methyl ester, 2-ethoxy-ethyl ester, butyl ester) (haloxyfop, -methyl, -P-methyl, -ethoxyethyl, -butyl), 3-cyclohexyl-6-dimethylamino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (4-chloro-2-methylsulphonyl-phenyl)-(5-cyclopropyl-isoxazol-4-yl)-methanone (isoxachlortole), (5-cyclopropyl-isoxazol-4-yl)-(2-methylsulphonyl-4-trifluoromethyl-phenyl)-methanone (isoxaflutole), 2-[2-[4-[(3,5-dichloro-2-pyridinyl)-oxy]-phenoxy]-1-oxo-propyl]-isoxazolidine (isoxapyrifop), (2-ethoxy-1-methyl-2-oxo-ethyl)-5-(2-chloro-4-trifluoromethyl-phenoxy)-2-nitro-benzoate (lactofen), N'-(3,4-dichloro-phenyl)-N-methoxy-N-methyl-urea (linuron), (4-chloro-2-methyl-phenoxy)-acetic acid (MCPA), 2-(4-chloro-2-methyl-phenoxy)-propionic acid (mecoprop), 2-(2-benzothiazolyloxy)-N-methyl-N-phenyl-acetamide (mefenacet), methyl 2-[[[[(4,6-dimethoxy-2-pyrimidinyl)amino]carbonyl]amino]sulphonyl]-4-[[(methylsulphonyl)amino]methyl]-benzoate (mesosulfuron), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), 2-chloro-N-(2,6-dimethyl-phenyl)-N-(1H-pyrazol-1-yl-methyl)-acetamide (metazachlor), N'-(3,4-dihydro-2-methoxy-2,4,4-trimethyl-2H-1-benzopyran-7-yl-oxy)-phenyl)-N-methoxy-N-methyl-urea (metobenzuron), N'-(4-bromophenyl)-N-methoxy-N-methyl urea (metobromuron), (S)-2-chloro-N-(2-ethyl-6-methyl-phenyl)-N-(2-methoxy-1-methylethyl)-acetamide (metolachlor, S-metolachlor), N-(2,6-dichloro-3-methyl-phenyl)-5,7-dimethoxy-1,2,4-triazolo[1,5-a]-pyrimidine-2-sulphonamide (metosulam), N'-(3-chloro-4-methoxy-phenyl)-N,N-dimethyl-urea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), S-ethyl-hexahydro-1H-azepine-1-carbothioate (molinate), 2-(2-naphthyloxy)-N-phenylpropanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), 4-chloro-5-methylamino-2-(3-trifluoromethylphenyl)-3(2H)-pyridazinone (norflurazon), S-(2-chloro-benzyl)-N,N-diethyl-thio-carbamate (orbencarb), 4-dipropylamino-3,5-dinitro-benzenesulphonamide (oryzalin), 3-[2,4-dichloro-5-(2-propinyloxy)-phenyl]-5-(t-butyl)-1,3,4-oxadiazol-2(3H)-one (oxadiargyl), 3-[2,4-dichloro-5-(1-methyl-ethoxy)-phenyl]-5-(t-butyl)-1,3,4-oxadiazol-2(3H)-one (oxadiazon), N-(4,6-dimethyl-pyrimidin-2-yl)-N'-(2-oxetan-3-yl-oxycarbonyl-phenylsulphonyl)-urea (oxasulfuron), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethylbenzene (oxyfluorfen), 1,1'-dimethyl-4,4'-bipyridinium (paraquat), 1-amino-N-(1-ethyl-propyl)-3,4-dimethyl-2,6-dinitro-benzene (pendimethalin), 4-(t-butyl)-N-(1-ethyl-propyl)-2,6-dinitro-benzenamine (pendralin), 4-amino-3,5,6-trichloro-pyridine-2-carboxylic acid (picloram), N-(4-fluoro-phenyl)-6-(3-trifluoromethyl-phenoxy)-pyridine-2-carboxamide (picolinafen), 2-chloro-N-(2,6-diethyl-phenyl)-N-(2-propoxy-ethyl)-acetamide (pretilachlor), N-(4,6-bis-difluoromethoxy-pyrimidin-2-yl)-N'-(2-methoxycarbonyl-phenylsulphonyl)-urea (primisulfuron-methyl), 1-chloro-N-[2-chloro-4-fluoro-5-[(6S,7aR)-6-fluorotetrahydro-1,3-dioxo-1H-pyrrolo[1,2-c]imidazol-2(3H)-yl]-phenyl]- methane-sulphonamide (profluazol), 2-chloro-N-isopropyl-N-phenyl-acetamide (propachlor), N-(3,4-dichloro-phenyl)-propanamide (propanil), (R)-[2-[[(1-methylethylidene)-amino]-oxy]-ethyl]-2-[4-(6-chloro-2-quinoxalinyloxy)-phenoxy]-propanoate (propaquizafop), 2-chloro-N-(2-ethyl-6-methyl-phenyl)-N-[(1-methyl-ethoxy)-methyl]-acetamide (propisochlor), methyl 2-[[[(4,5-dihydro-4-methyl-5-oxo-3-propoxy-1H-1,2,4-triazol-1-yl]-carbonyl]-amino]-sulphonyl]-benzoate sodium salt (propoxy-carbazone-sodium), S-phenylmethyl N,N-dipropyl-thiocarbamate (prosulfocarb), N-(4-methoxy-6-methyl-1,3,5-triazin-2-yl)-N'-(2-(3,3,3-trifluoro-propyl)-phenylsulphonyl)-urea (prosulfuron), ethyl [2-chloro-5-(4-chloro-5-difluoromethoxy-1-methyl-1H-pyrazol-3-yl)-4-fluoro-phenoxy]-acetate (pyraflufen-ethyl), 1-(3-chloro-4,5,6,7-tetrahydro-pyrazolo[1,5-a]pyridin-2-yl)-5-(methyl-2-propinylamino)-1H-pyrazole-4-carbonitrile (pyrazogyl), 4-(2,4-dichloro-benzoyl)-1,3-dimethyl-5-(4-methyl-phenylsulphonyloxy)-pyrazole (pyrazolate), 4-(2,4-dichloro-benzoyl)-1,3-dimethyl-5-(phenylcarbonylmethoxy)-pyrazole (pyrazoxyfen), N-(4,6-dimethoxy-pyrimidin-2-yl)-N'-(4-ethoxycarbonyl-1-methyl-pyrazol-5-yl-sulphonyl)-urea (pyrazosulfuronethyl), O-[2,6-bis-(4,6-dimethoxy-pyrimidin-2-yl-oxy)-benzoyl] diphenylmethanone-oxime (pyribenzoxim), 6-chloro-3-phenyl-4-pyridazinol (pyridafol), O-(6-chloro-3-phenyl-pyridazin-4-yl)-S-octyl thiocarbonate (pyridate), 6-chloro-3-phenyl-pyridazin-4-ol (pyridatol), 7-[(4,6-dimethoxy-2-pyrimidinyl)-thio]-3-methyl-1(3H)-isobenzofuranone (Pyriftalid), methyl 2-(4,6-dimethoxy-pyrimidin-2-yl-oxy)-benzoate (pyriminobac-methyl), 2-chloro-6-(4,6-dimethoxy-pyrimidin-2-ylthio)-benzoic acid sodium salt (pyrithiobac-sodium), 3,7-dichloro-quinoline-8-carboxylic acid (quinchlorac), 7-chloro-3-methyl-quinoline-8-carboxylic acid (quinmerac), 2-[4-(6-chloro-2-quinoxalinyloxy)-phenoxy]-propanoic acid (ethyl ester, tetrahydro-2-furanyl-methyl ester) (quizalofop, -ethyl, -P-ethyl, -P-tefuryl), N-(4,6-dimethoxy-pyrimidin-2-yl)-N'-(3-ethylsulphonyl-pyridin-2-yl-sulphonyl)-urea (rimsulfuron), 2-(1-ethoximinobutyl)-5-(2-ethylthiopropyl)-3-hydroxy-2-cyclohexen-1-one (sethoxydim), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone), methyl 2-[[[[(4,6-dimethyl-2-pyrimidinyl)amino]carbonyl]amino]sulphonyl]-benzoate (sulfometuron-methyl), N-phosphonomethyl-glycine-trimethylsulphonium (sulfosate), N-(4,6-dimethoxy-pyrimidin-2-yl)-N'-(2-ethylsulphonyl)-imidazo[1,2-a]pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), methyl 2-difluoromethyl-5-(4,5-dihydro-thiazol-2-yl)-4-(2-methyl-propyl)-6-trifluoromethyl-pyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxy-carbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diiso-propylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), (3,5,6-trichloro)-pyridin-2-yl-oxy-acetic acid (triclopyr), 2-(3,5-dichloro-phenyl)-2-(2,2,2-trichloro-ethyl)-oxirane (tridiphane), N-[[(4,6-dimethoxy-2-pyrimidinyl)-amino]-carbonyl]-3-(2,2,2-trifluoro-ethoxy)-2-pyridinesulphonamide sodium salt (trifloxysulfuron), 1-amino-2,6-dinitro-N,N-dipropyl-4-trifluoromethyl-benzene (trifluralin), N-[4-dimethylamino-6-(2,2,2-trifluoro-ethoxy)-1,3,5-triazin-2-yl]-N'-(2-methoxycarbonyl-phenylsulphonyl)-urea (triflusulfuron-methyl), N-(4-methoxy-6-trifluoromethoxy-1,3,5-triazin-2-yl)-N'-(2-trifluoromethyl-phenylsulphonyl)-urea (tritosulfuron), N-[[(4,6-dimethoxy-2-pyrimidinyl)-amino]-carbonyl]-3-(N-methyl-N-methylsulphonyl-amino)-2-pyridinesulphonamide, (cf. WO-A-92/10660), 4-[4,5-dihydro-4-methyl-5-oxo-(3-trifluoromethyl)-1H-1,2,4-triazol-1-yl]-2-[(ethylsulphonyl)amino]-5-fluoro-benzene-carbothioamide (cf. WO-A-95/30661)

("Active Compounds of Group 2"), and/or (c) a compound which improves crop plant compatibility, from the group of compounds below:
4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (BAS-145138), 4-dichloro-acetyl-3,4-dihydro-3-methyl-2H-1,4-benzoxazine (benoxacor), 1-methyl-hexyl 5-chloro-quinoxalin-8-oxy-acetate (cloquintocet-mexyl), α-(cyanomethoximino)-phenylacetonitrile (cyometrinil), 2,4-dichlorophenoxy-acetic acid (2,4-D), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), N-(4-methyl-phenyl)-N'-(1-methyl-1-phenyl-ethyl)-urea (dymron), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), (4-chloro-2-methyl-phenoxy)-acetic acid (MCPA), (+-)-2-(4-chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, α-(1,3-dioxolan-2-yl-methoximino)-phenylacetonitrile (oxabetrinil), 2,2-dichloro-N-(1, 3-dioxolan-2-yl-methyl)-N-(2-propenyl)-acetamide (PPG-1292), 3-dichloroacetyl-2,2,5-trimethyl-oxazolidine (R-29148), N-cyclopropyl-4-[[(2-methoxy-5-methylbenzoyl)-amino]-sulphonyl]-benzamide, (WO-A-99/66795), N-[(4-methoxyacetylamino)-phenyl]-sulphonyl-2-methoxy-benzamide (WO-A-99/66795) and N-[(4-methylaminocarbonylamino)-phenyl]-sulphonyl-2-methoxy-benzamide (WO-A-99/66795).

("Active Compounds of Group 3").

Preferred meanings of the radicals listed in the formula (I) shown above are illustrated below.

$R^1$ preferably represents hydrogen, amino or in each case optionally cyano-, fluorine-, chlorine- methoxy- or ethoxy-substituted methyl, ethyl, n- or i-propyl.

$R^2$ preferably represents in each case optionally fluorine- and/or chlorine-substituted methyl, ethyl, n- or i-propyl.

$R^3$ preferably represents hydrogen, fluorine, chlorine, bromine or in each case optionally fluorine- and/or chlorine-substituted methyl, ethyl, n- or i-propyl.

$R^4$ preferably represents hydrogen, cyano, fluorine, chlorine or bromine.

$R^5$ preferably represents cyano, thiocarbamoyl, fluorine, chlorine or bromine.

$R^6$ preferably represents nitro, cyano, carboxyl, carbamoyl, thiocarbamoyl, hydroxyl, mercapto, amino, hydroxyamino, aminosulphonyl, fluorine, chlorine, bromine, represents in each case optionally cyano-, carboxyl-, hydroxyl-, methoxy-, ethoxy-, n- or i-propoxy-, acetyl-, propionyl-, n- or i-butyroyl-, methoxycarbonyl-, ethoxycarbonyl-, n- or i-propoxycarbonyl-, allyloxycarbonyl- or propargyloxycarbonyl-substituted methyl, ethyl, n- or i-propyl, n-, i- or s-butyl, methoxy, ethoxy, n- or i-propoxy, n-, i- or s-butoxy, methylthio, ethylthio, n- or i-propylthio, n-, i- or s-butylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, n-, i- or s-butylamino, represents in each case optionally cyano-, carboxyl-, fluorine-, chlorine-, bromine-, methoxycarbonyl- and/or ethoxycarbonyl-substituted ethenyl, propenyl, butenyl, ethinyl, propinyl, butinyl, propenyloxy, butenyloxy, propinyloxy or butinyloxy, represents in each case optionally fluorine- and/or chlorine-, methoxy-, ethoxy-, n- or i-propoxy-substituted acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylaamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-methylsulphonyl-N-n-propylsulphonyl-amino, N-methylsulphonyl-N-i-propylsulphonyl-amino, N-acetyl-N-methylsulphonylamino, N-propionyl-N-methylsulphonyl-amino, N-n-butyroyl-N-methylsulphonyl-amino, N-i-butyroyl-N-methylsulphonyl-amino, N-s-butyroyl-N-methylsulphonyl-amino, N-t-butyroyl-N-methylsulphonyl-amino, N-(2,2-dimethyl-propanoyl)-N-ethylsulphonyl-amino, N-(2-methylpropanoyl)-N-ethylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, N-s-butyroyl-N-ethylsulphonyl-amino, N-t-butyroyl-N-ethylsulphonyl-amino, or represents in each case optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino.

$R^1$ particularly preferably represents hydrogen, amino, methyl or ethyl.

$R^2$ particularly preferably represents in each case fluorine- and/or chlorine-substituted methyl or ethyl.

$R^3$ particularly preferably represents hydrogen, fluorine, chlorine, bromine or in each case optionally fluorine- and/or chlorine-substituted methyl or ethyl.

$R^4$ particularly preferably represents hydrogen, fluorine or chlorine.

$R^5$ particularly preferably represents cyano, thiocarbamoyl, chlorine or bromine.

$R^6$ particularly preferably represents nitro, cyano, carboxyl, carbamoyl, thiocarbamoyl, hydroxyl, mercapto, amino, hydroxyamino, aminosulphonyl, fluorine, chlorine, bromine, represents in each case optionally cyano-, carboxyl-, hydroxyl-, methoxy-, ethoxy-, acetyl-, propionyl-, methoxycarbonyl- and/or ethoxycarbonyl, n- or i-propoxycarbonyl-, allyloxycarbonyl- or propargyl-oxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, represents in each case optionally cyano-, carboxyl-, fluorine-, chlorine-, bromine-, methoxycarbonyl- and/or ethoxycarbonyl-substituted ethenyl, propenyl, ethinyl, propinyl, propenyloxy or propinyloxy, represents in each case optionally fluorine- and/or chlorine-, methoxy- or ethoxy-substituted acetylamino, propionylamino, methoxycarbonylamino, ethoxycarbonylamino, methylsulphonylamino, ethylsulphonylamino, n- or i-propylsulphonylamino, n-, i-, s- or t-butylsulphonylamino, N,N-bis-methylsulphonyl-amino, N,N-bis-ethylsulphonylamino, N-ethylsulphonyl-N-methylsulphonyl-amino, N-methylsulphonyl-N-n-propylsulphonyl-amino, N-methylsulphonyl-N-i-propylsulphonyl-amino, N-acetyl-N-methylsulphonyl-amino, N-propionyl-N-methylsulphonyl-amino, N-(2,2-dimethyl-propanoyl)-N-ethylsulphonyl-amino, N-(2-methylpropanoyl)-N-ethylsulphonyl-amino, N-n-butyroyl-N-methylsulphonyl-amino, N-i-butyroyl-N-methylsulphonyl-amino, N-s-butyroyl-N-methylsulphonyl-amino, N-t-butyroyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, N-s-butyroyl-N-ethylsulphonyl-amino, N-t-butyroyl-N-ethylsulphonyl-amino, or represents in each case optionally cyano-, fluorine-, chlorine-, bromine-, methyl-, ethyl-, trifluoromethyl-, methoxy-, ethoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino.

Very particularly preferred components of the active compound combinations according to the invention are compounds of the formula (I) in which $R^1$ represents amino, $R^2$ represents trifluoromethyl, $R^3$ represents hydrogen, chlorine or methyl, $R^4$ represents fluorine, $R^5$ represents cyano or thiocarbamoyl, and $R^6$ represents in each case optionally fluorine- and/or chlorine-substituted methylsulphonylamino, ethylsulphonylaamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-methylsulphonyl-N-n-propylsulphonyl-amino, N-methylsulphonyl-N-i-propylsulphonyl-amino, N-acetyl-N-methylsulphonyl-amino, N-propionyl-N-methylsulphonyl-amino, N-(2,2-dimethyl-propanoyl)-N-ethylsulphonyl-amino, N-(2-methylpropanoyl)-N-ethylsulphonyl-amino, N-n-butyroyl-N-methylsulphonyl-amino, N-i-butyroyl-N-methylsulphonyl-amino, N-s-butyroyl-N-methylsulphonyl-amino, N-t-butyroyl-N-methylsulphonyl-amino, N-methoxyacetyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, N-s-butyroyl-N-ethylsulphonyl-amino, N-t-butyroyl-N-ethylsulphonyl-amino, N-methoxyacetyl-N-ethylsulphonylamino, or represents in each case optionally cyano-, fluoro-, chlorine-, bromine-, methyl-, ethyl-, Trifluoromethyl-, methoxy-, ethoxy-, difluoromethoxy- or trifluoromethoxy-substituted N-phenylcarbonyl-N-methylsulphonylamino, N-phenylcarbonyl-N-ethylsulphonyl-amino, N-thienylcarbonyl-N-methylsulphonyl-amino or N-thienylcarbonyl-N-ethylsulphonyl-amino.

Other very particularly preferred components of the active compound combinations according to the invention are compounds of the formula (I) in which $R^1$ represents methyl, $R^2$ represents trifluoromethyl, $R^3$ represents hydrogen, chlorine or methyl, $R^4$ represents fluorine, $R^5$ represents thiocarbamoyl, and $R^6$ represents in each case optionally fluorine- and/or chlorine-substituted methylsulphonylamino, ethylsulphonylamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-methylsulphonyl-N-n-propylsulphonyl-amino, N-methylsulphonyl-N-i-propylsulphonyl-amino, N-acetyl-N-methylsulphonyl-amino, N-propionyl-N-methylsulphonyl-amino, N-(2,2-dimethyl-propanoyl)-N-ethylsulphonyl-amino, N-(2-methylpropanoyl)-N-ethylsulphonyl-amino, N-n-butyroyl-N-methylsulphonyl-amino, N-i-butyroyl-N-methylsulphonyl-amino, N-s-butyroyl-N-methylsulphonyl-amino, N-t-butyroyl-N-methylsulphonyl-amino, N-methoxyacetyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, N-s-butyroyl-N-ethylsulphonyl-amino, N-t-butyroyl-N-ethylsulphonyl-amino, N-methoxyacetyl-N-ethylsulphonylamino, or represents in each case optionally cyano-, fluorine-, chlorine-, bromine-, methyl-, ethyl-, trifluoromethyl-, methoxy-, ethoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino.

Other very particularly preferred components of the active compound combinations according to the invention are compounds of the formula (I) in which $R^1$ represents amino or methyl, $R^2$ represents trifluoromethyl, $R^3$ represents hydrogen, chlorine or methyl, $R^4$ represents hydrogen, fluorine or chlorine, $R^5$ represents cyano, thiocarbamoyl or chlorine, and $R^6$ represents carboxyl, carbamoyl, thiocarbamoyl, hydroxyl, mercapto, amino, fluorine, chlorine, bromine, represents in each case optionally cyano-, carboxyl-, hydroxyl-, methoxy-, ethoxy-, acetyl-, propionyl-, methoxycarbonyl-, ethoxycarbonyl-, n- or i-propoxycarbonyl-, allyloxycarbonyl- or propargyloxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, N-(2,2-dimethyl-propanoyl)-N-ethylsulphonyl-amino, N-(2-methyl-propanoyl)-N-ethylsulphonyl-amino, or represents in each case optionally cyano-, carboxyl-, fluorine-, chlorine-, bromine-, methoxycarbonyl- and/or ethoxycarbonyl-substituted ethenyl, propenyl, ethinyl, propinyl, propenyloxy or propinyloxy.

Examples of the compounds of the formula (I) which may be mentioned and can be used as mixing partners according to the invention are:

5-fluoro-4-(3-methyl-2,6-dioxo-4-trifluoromethyl-3,6-dihydro-1(2H)-pyrimidinyl)-2-methoxy-benzonitrile 5-fluoro-4-(3-methyl-2,6-dioxo-4-trifluoromethyl-3,6-dihydro-1(2H)-pyrimidinyl)-2-ethoxy-benzonitrile 5-fluoro-4-(3-methyl-2,6-dioxo-4-trifluoromethyl-3,6-dihydro-1(2H)-pyrimidinyl)-2-n-propoxy-benzonitrile 5-fluoro-4-(3-methyl-2,6-dioxo-4-trifluoromethyl-3,6-dihydro-1(2H)-pyrimidinyl)-2-i-propoxy-benzonitrile 5-fluoro-4-(3-methyl-2,6-dioxo-4-trifluoromethyl-3,6-dihydro-1(2H)-pyrimidinyl)-2-n-butoxy-benzonitrile 5-fluoro-4-(3-methyl-2,6-dioxo-4-trifluoromethyl-3,6-dihydro-1(2H)-pyrimidinyl)-2-i-butoxy-benzonitrile 5-fluoro-4-(3-methyl-2,6-dioxo-4-trifluoromethyl-3,6-dihydro-1(2H)-pyrimidinyl)-2-s-butoxy-benzonitrile 5-fluoro-4-(3-methyl-2,6-dioxo-4-trifluoromethyl-3,6-dihydro-1(2H)-pyrimidinyl)-2-allyloxy-benzonitrile 5-fluoro-4-(3-methyl-2,6-dioxo-4-trifluoromethyl-3,6-dihydro-1(2H)-pyrimidinyl)-2-propargyloxy-benzonitrile 5-fluoro-4-(3-methyl-2,6-dioxo-4-trifluoromethyl-3,6-dihydro-1(2H)-pyrimidinyl)-2-[(1-methyl-2-propinyl)-oxy]-benzonitrile methyl 2-chloro-5-(3,6-dihydro-3-methyl-2,6-dioxo-4-trifluoromethyl-1(2H)-pyrimidinyl)-benzoate ethyl 2-chloro-5-(3,6-dihydro-3-methyl-2,6-dioxo-4-trifluoromethyl-1(2H)-pyrimidinyl)-benzoate n-propyl 2-chloro-5-(3,6-dihydro-3-methyl-2,6-dioxo-4-trifluoromethyl-1(2H)-pyrimidinyl)-benzoate i-propyl 2-chloro-5-(3,6-dihydro-3-methyl-2,6-dioxo-4-trifluoromethyl-1(2H)-pyrimidinyl)-benzoate

[1,1-dimethyl-2-oxo-2-(2-propenyloxy)]-ethyl]2-chloro-5-(3,6-dihydro-3-methyl-2,6-dioxo-4-trifluoromethyl-1(2H)-pyrimidinyl)-benzoate 2-(methylsulphonylamino)-5-fluoro-4-[3-methyl-2,6-dioxo-4-trifluoromethyl-3,6-dihydro-1(2H)-pyrimidinyl]-benzenecarbothioamide 2-(ethylsulphonylamino)-5-fluoro-4-[3-methyl-2,6-dioxo-4-trifluoromethyl-3,6-dihydro-1(2H)-pyrimidinyl]-benzenecarbothioamide 2-(n-propylsulphonylamino)-5-fluoro-4-[3-methyl-2,6-dioxo-4-trifluoromethyl-3,6-dihydro-1(2H)-pyrimidinyl]-benzenecarbothioamide 2-(i-propylsulphonylamino)-5-fluoro-4-[3-methyl-2,6-dioxo-4-trifluoromethyl-3,6-dihydro-1(2H)-pyrimidinyl]-benzenecarbothioamide 2-(n-butylsulphonylamino)-5-fluoro-4-[3-methyl-2,6-dioxo-4-trifluoromethyl-3,6-dihydro-1(2H)-pyrimidinyl]-benzenecarbothioamide N-[2-cyano-4-fluoro-5-(3-methyl-2,6-dioxo-4-trifluoromethyl-3,6-dihydro-1(2H)-pyrimidinyl)-phenyl]-N-(acetyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(methylsulphonyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(ethylsulphonyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(ethylsulphonyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(n-propylsulphonyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(i-propylsulphonyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(acetyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(acetyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(propanoyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(propanoyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(2-methyl-propanoyl)-1-methanesulphonamide N-[2-cyano-4-fluoro-5-(3-methyl-2,6-dioxo-4-trifluoromethyl-3,6-dihydro-1(2-pyrimidinyl)-phenyl]-N-(2-methyl-propanoyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(butanoyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(butanoyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(2-methyl-butanoyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(2-methyl-butanoyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(2,2-dimethyl-propanoyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(2,2-dimethyl-propanoyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(methoxyacetyl)-1-methanesulphonamide N-[2-cyano-4-fluoro-5-(3-methyl-2,6-dioxo-4-trifluoromethyl-3,6-dihydro-1(2H)-pyrimidinyl)-phenyl]-N-(methoxyacetyl)-1-ethanesulphonamide N-[2-cyano-4-fluoro-5-(3-methyl-2,6-dioxo-4-trifluoromethyl-3,6-dihydro-1(2H)-pyrimidinyl)-phenyl]-N-(4-methoxy-benzoyl)-ethanesulphonamide N-[5-(3-amino-2,6-dioxo-4-trifluoromethyl-3,6-dihydro-1(2H)-pyrimidinyl)-2-cyano-4-fluoro-phenyl]-N-benzoyl-1-methanesulphonamide N-[5-(3-amino-2,6-dioxo-4-trifluoromethyl-3,6-dihydro-1(2H)-pyrimidinyl)-2-cyano-4-fluoro-phenyl]-N-benzoyl-1-ethanesulphonamide N-[5-(3-amino-2,6-dioxo-4-trifluoromethyl-3,6-dihydro-1(2H)-pyrimidinyl)-2-cyano-4-fluoro-phenyl]-N-(4-methoxy-benzoyl)-1-methanesulphonamide N-[5-(3-amino-2,6-dioxo-4-trifluoromethyl-3,6-dihydro-1(2H)-pyrimidinyl)-2-cyano-4-fluoro-phenyl]-N-(2-thienyl-carbonyl)-1-methanesulphonamide N-[5-(3-amino-2,6-dioxo-4-trifluoromethyl-3,6-dihydro-1(2H)-pyrimidinyl)-2-cyano-4-fluoro-phenyl]-N-(2-thienyl-carbonyl)-1-ethanesulphonamide Particular emphasis is given to the compound [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (I-1)—CAS-Reg.No.: 134605-64-4—as mixing component of the formula (I) (WO 91/00278).

Particular emphasis is likewise given to the compound 5-fluoro-4-(3-methyl-2,6-dioxo-4-trifluoromethyl-3,6-dihydro-1(2H)-pyrimidinyl)-2-[(1-methyl-2-propinyl)-oxy]-benzonitrile (I-2)—CAS-Reg.No.: 186605-50-5—as mixing component of the formula (I) (WO 97/01541).

Particular emphasis is likewise given to the compound N-[2-cyano-4-fluoro-5-(3-methyl-2,6-dioxo-4-trifluoromethyl-3,6-dihydro-1(2H)-pyrimidinyl)-phenyl]-N-(2,2-dimethyl-propanoyl)-1-ethanesulphonamide (I-3)—according to Chem. Abstracts also to be referred to as N-[2-cyano-5-(3,6-dihydro-3-methyl-2,6-dioxo-4-trifluoromethyl-1(2H)-pyrimidinyl)-4-fluoro-phenyl]-N-ethylsulphonyl-2,2-dimethylpropanamide (CAS-Reg.-No.: 232262-67-8)—as mixing component of the formula (I) (WO 95/29168).

Particular emphasis is likewise given to the compound N-[2-cyano-4-fluoro-5-(3-methyl-2,6-dioxo-4-trifluoromethyl-3,6-dihydro-1(2H)-pyrimidinyl)-phenyl]-

N-(4-methoxy-benzoyl)-ethanesulphonamide (I-4)—according to Chem. Abstracts also to be referred to as N-[2-cyano-5-(3,6-dihydro-3-methyl-2,6-dioxo-4-trifluoromethyl-1(2H)-pyrimidinyl)-4-fluoro-phenyl]-N-ethylsulphonyl-4-methoxy-benzamide (CAS-Reg.-No.: 184293-08-1)—as mixing component of the formula (I) (WO 96/35679).

Particular emphasis is likewise given to the compound N-[5-(3-amino-2,6-dioxo-4-trifluoromethyl-3,6-dihydro-1 (2H)-pyrimidinyl)-2-cyano-4-fluoro-phenyl]-N-(2-thienyl-carbonyl)-1-ethanesulphonamide (I-5)—according to Chem. Abstracts also to be referred to as N-[2-cyano-5-(3, 6-dihydro-3-methyl-2,6-dioxo-4-trifluoromethyl-1(2H)-pyrimidinyl)-4-fluoro-phenyl]-N-ethylsulphonyl-2-thiophene-carboxamide—as mixing component of the formula (I) (WO 96/35679).

Particular emphasis is likewise given to the compound 2-(ethylsulphonylamino)-5-fluoro-4-[3-methyl-2,6-dioxo-4-trifluoromethyl-3,6-dihydro-1(2H)-pyrimidinyl]-benzenecarbothioamide (I-6)—according to Chem. Abstracts also to be referred to as 4-(3,6-dihydro-3-methyl-2,6-dioxo-4-trifluoromethyl-1(2H)-pyrimidinyl)-2-ethyl-sulphonylamino-5-fluoro-benzenecarbothioamide (CAS-Reg.-No.: 173980-09-1)—as mixing component of the formula (I) (WO 95/30661).

The compounds of the formula (I) are described in the patent applications or patents mentioned above for the N-aryl-uracils.

According to their chemical structure, the active compounds of Group 2 can be classified under the following classes of active compounds.

Amides (for example isoxaben, picolinafen, propanil), arylheterocycles (for example azafenidin, benzfendizone, butafenacil-allyl, carfentrazone-ethyl, cinidon-ethyl, fluazolate, flumiclorac-pentyl, flumioxazin, flupropacil, fluthiacet-methyl, oxadiazon, oxadiargyl, profluazol, pyraflufen-ethyl, pyridate, pyridafol, sulfentrazone, thidiazimin, 4-[4,5-dihydro-4-methyl-5-oxo-(3-trifluoromethyl)-1H-1,2,4-triazol-1-yl]-2-[(ethylsulphonyl)amino]-5-fluoro-benzenecarboxamide), aryloxyphenoxy-propionates (for example clodinafop-propargyl, cyhalofop-butyl, diclofop-methyl, fenoxaprop-P-ethyl, fluazifop-P-butyl, haloxyfop-R-methyl, quizalofop-P-ethyl), carboxylic acid derivatives (for example clopyralid, dicamba, fluroxypyr, picloram, triclopyr), benzothiadiazoles (for example bentazon), chloroacetamides (for example acetochlor, alachlor, butachlor, (S-) dimethenamid, metazachlor, metolachlor, pretilachlor, propachlor, propisochlor), cyclohexanediones (for example butroxydim, clefoxydim, cycloxydim, sethoxydim, tralkoxydim), dinitroanilines (for example benfluralin, ethalfluralin, oryzalin, pendimethalin, trifluralin), diphenyl ethers (for example acifluorfen-sodium, aclonifen, bifenox, fluoroglycofen-ethyl, fomesafen, lactofen, oxyfluorfen), ureas (for example chlortoluron, diuron, isoproturon, linuron, metobromuron, metoxuron), imidazolinones (for example imazamethabenz-methyl, imazamox, imazaquin, imazethapyr), isoxazoles (for example isoxaflutole), nicotinanilides (for example diflufenican), nitriles (for example bromoxynil, ioxynil), organophosphorus compounds (for example glufosinate-ammonium, glyphosate-isopropylammonium, sulfosate), oxyacetamides (for example flufenacet, mefenacet), phenoxycarboxylic acid derivatives (for example 2,4-D, dichlorprop-P, MCPA, MCPB, mecoprop), pyrazoles (for example pyrazolate, pyrazoxyfen), pyridazinones (for example norflurazon), pyridines (for example dithiopyr, thiazopyr), pyrimidinyl(thio)benzoates (for example bispyribac, pyribenzoxim, pyrithiobac, pyriminobac), sulphonylureas (for example amidosulfuron, azimsulfuron, bensulfuron-methyl, chlorimuron-ethyl, chlorsulfuron, cinosulfuron, cyclosulfamuron, ethoxysulfuron, flupyrsulfuron-methyl-sodium, foramsulfuron, iodosulfuron-methyl-sodium, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron), tetrazolinones (for example fentrazamide), thiocarbamates (for example butylate, dimepiperate, EPTC, esprocarb, molinate, orbencarb, prosulfocarb, triallate), triazines (for example ametryn, atrazine, cyanazine, dimexyflam, simazin, terbuthylazine, terbutryn), triazinones (for example hexazinone, metamitron, metribuzin), triazoles (for example amitrole), triazolinones (for example amicarbazone, flucarbazone-sodium, propoxycarbazone-sodium), triazolopyrimidines (for example cloransulam-methyl, diclosulam, florasulam, flumetsulam, metosulam), triketones (for example mesotrione, sulcotrione), uracils (for example bromacil).

Mixing components from the active compounds of Group 2 which are particularly emphasized are:

acetochlor, alachlor, amicarbazone, amitrole, atrazine, bromacil, carfentrazone-ethyl, chlorimuron-ethyl, clodinafop-propargyl, cyanazine, diclosulam, dimethenamid, S-dimethenamid, diuron, EPTC, fenoxaprop-P-ethyl, fentrazamide, flucarbazone-sodium, flufenacet, flumetsulam, glufosinate-ammonium, glyphosate-isopropylammonium, imazamox, imazaquin, imazethapyr, isoxaflutole, mesotrione, metolachlor, S-metolachlor, metosulam, metribuzin, nicosulfuron, norflurazon, pendimethalin, propoxycarbazone-sodium, rimsulfuron, simazin, sulfometuron-methyl, sulcotrione, sulfentrazone, sulfosate, terbuthylazine, thifensulfuron-methyl, trifluralin, 4-[4,5-dihydro-4-methyl-5-oxo-(3-trifluoromethyl)-1H-1,2,4-triazol-1-yl]-2-[(ethylsulphonyl)amino]-5-fluoro-benzenecarbothioamide.

According to their chemical structure, the particularly emphasized active compounds of the Group 2 can be classified under the following classes of active compounds:

Arylheterocycles (for example carfentrazone-ethyl, sulfentrazone, 4-[4,5-dihydro-4-methyl-5-oxo-(3-trifluoromethyl)-1H-1,2,4-triazol-1-yl]-2-[(ethylsulphonyl)-amino]-5-fluoro-benzenecarbothioamide), chloroacetamides (for example acetochlor, alachlor, dimethenamid, S-dimethenamid, metolachlor, S-metolachlor), dinitroanilines (for example pendimethalin, trifluralin), ureas (for example diuron), imidazolinones (for example imazamox, imazaquin, imazethapyr), organophosphorus compounds (for example glufosinate, glyphosate, sulfosate), oxyacetamides (for example flufenacet), pyridazinones (for example norflurazon), sulfonylureas (for example chlorimuron-ethyl, nicosulfuron, rimsulfuron, sulfometuron-methyl, thifensulfuron-methyl), tetrazolinones (for example fentrazamide), triazines (for example atrazine, cyanazine, simazine, terbuthylazine), triazinones (for example metribuzin), triazolinones (for example amicarbazone, flucarbazone-sodium, propoxycarbazone-sodium), triazolopyrimidines (for example diclosulam, florasulam, metosulam), triketones (for example mesotrione, sulcotrione), uracils (for example bromacil).

The compositions according to the invention may comprise one or two active compounds of Group 1 and one active compound of Group 3.

The compositions according to the invention preferably comprise one or two active compounds of Group 1, one to three active compounds of Group 2 and optionally one active compound of Group 3.

In particular, the compositions according to the invention comprise one active compound of Group 1, one or two active compounds of Group 2 and optionally one active compound of Group 3.

Examples of combinations according to the invention comprising in each case one active compound of Group 1 and two active compounds of Group 2 (preferably selected from the group of the photosynthesis inhibitors on the one hand and the group of the acetyl-CoA-carboxylase inhibitors on the other hand)—or in each case one active compound of Group 1, two active compounds of Group 2 and one compound of Group 3- are listed in Table 1 below.

TABLE 1

| Active compound Group 1 | First active compound of Group 2 | Second active compound of Group 2 (if appropriate + additional active compound of Group 3) |
|---|---|---|
| I-1 | amicarbazone | clodinafop-propargyl |
| I-1 | amicarbazone | clodinafop-propargyl + cloquintocet-mexyl |
| I-1 | amicarbazone | fenoxaprop-P-ethyl |
| I-1 | amicarbazone | fenoxaprop-P-ethyl + mefenpyr-diethyl |
| I-1 | amicarbazone | flucarbazone-sodium |
| I-1 | amicarbazone | propoxycarbazone-sodium |
| I-1 | amicarbazone | alachlor |
| I-1 | amicarbazone | dimethenamid |
| I-1 | amicarbazone | S-dimethenamid |
| I-1 | amicarbazone | metolachlor |
| I-1 | amicarbazone | metolachlor + benoxacor |
| I-1 | amicarbazone | S-metolachlor |
| I-1 | amicarbazone | S-metolachlor + benoxacor |
| I-1 | amicarbazone | acetochlor |
| I-1 | amicarbazone | acetochlor + dichlormid |
| I-1 | amicarbazone | acetochlor + R-29148 |
| I-1 | amicarbazone | flufenacet |
| I-1 | atrazine | clodinafop-propargyl |
| I-1 | atrazine | clodinafop-propargyl + cloquintocet-mexyl |
| I-1 | atrazine | fenoxaprop-P-ethyl |
| I-1 | atrazine | fenoxaprop-P-ethyl + mefenpyr-diethyl |
| I-1 | atrazine | flucarbazone-sodium |
| I-1 | atrazine | propoxycarbazone-sodium |
| I-1 | atrazine | alachlor |
| I-1 | atrazine | dimethenamid |
| I-1 | atrazine | S-dimethenamid |
| I-1 | atrazine | acetochlor |
| I-1 | atrazine | acetochlor + dichlormid |
| I-1 | atrazine | acetochlor + R-29148 |
| I-1 | atrazine | flufenacet |
| I-1 | atrazine | metolachlor |
| I-1 | atrazine | metolachlor + benoxacor |
| I-1 | atrazine | S-metolachlor |
| I-1 | atrazine | S-metolachlor + benoxacor |
| I-1 | metribuzin | clodinafop-propargyl |
| I-1 | metribuzin | clodinafop-propargyl + cloquintocet-mexyl |
| I-1 | metribuzin | fenoxaprop-P-ethyl |
| I-1 | metribuzin | fenoxaprop-P-ethyl + mefenpyr-diethyl |
| I-1 | metribuzin | flucarbazone-sodium |
| I-1 | metribuzin | propoxycarbazone-sodium |
| I-1 | metribuzin | alachlor |
| I-1 | metribuzin | dimethenamid |
| I-1 | metribuzin | S-dimethenamid |
| I-1 | metribuzin | metolachlor |
| I-1 | metribuzin | metolachlor + benoxacor |
| I-1 | metribuzin | metolachlor |
| I-1 | metribuzin | metolachlor + benoxacor |
| I-1 | metribuzin | acetochlor |
| I-1 | metribuzin | acetochlor + dichlormid |
| I-1 | metribuzin | acetochlor + R-29148 |
| I-1 | metribuzin | acetochlor + furilazone |
| I-1 | metribuzin | flufenacet |
| I-1 | terbuthylazine | clodinafop-propargyl |
| I-1 | terbuthylazine | clodinafop-propargyl + cloquintocet-mexyl |
| I-1 | terbuthylazine | fenoxaprop-P-ethyl |
| I-1 | terbuthylazine | fenoxaprop-P-ethyl + mefenpyr-diethyl |
| I-1 | terbuthylazine | flucarbazone-sodium |
| I-1 | terbuthylazine | propoxycarbazone-sodium |
| I-1 | terbuthylazine | alachlor |
| I-1 | terbuthylazine | dimethenamid |
| I-1 | terbuthylazine | S-dimethenamid |
| I-1 | terbuthylazine | acetochlor |
| I-1 | terbuthylazine | acetochlor + dichlormid |
| I-1 | terbuthylazine | acetochlor + R-29148 |
| I-1 | terbuthylazine | acetochlor + furilazole |
| I-1 | terbuthylazine | flufenacet |
| I-1 | simazine | clodinafop-propargyl |
| I-1 | simazine | clodinafop-propargyl + cloquintocet-mexyl |
| I-1 | simazine | fenoxaprop-P-ethyl |
| I-1 | simazine | fenoxaprop-P-ethyl + mefenpyr-diethyl |
| I-1 | simazine | flucarbazone-sodium |
| I-1 | simazine | propoxycarbazone-sodium |
| I-1 | simazine | alachlor |
| I-1 | simazine | dimethenamid |
| I-1 | simazine | S-dimethenamid |
| I-1 | simazine | metolachlor |
| I-1 | simazine | metolachlor + benoxacor |
| I-1 | simazine | S-metolachlor |
| I-1 | simazine | S-metolachlor + benoxacor |
| I-1 | simazine | acetochlor |
| I-1 | simazine | acetochlor + dichlormid |
| I-1 | simazine | acetochlor + R-29148 |
| I-1 | simazine | acetochlor + furilazole |
| I-1 | simazine | flufenacet |
| I-1 | cyanazine | clodinafop-propargyl |
| I-1 | cyanazine | clodinafop-propargyl + cloquintocet-mexyl |
| I-1 | cyanazine | fenoxaprop-P-ethyl |
| I-1 | cyanazine | fenoxaprop-P-ethyl + mefenpyr-diethyl |
| I-1 | cyanazine | flucarbazone-sodium |
| I-1 | cyanazine | propoxycarbazone-sodium |
| I-1 | cyanazine | alachlor |
| I-1 | cyanazine | dimethenamid |
| I-1 | cyanazine | S-dimethenamid |
| I-1 | cyanazine | metolachlor |
| I-1 | cyanazine | metolachlor + benoxacor |
| I-1 | cyanazine | S-metolachlor |
| I-1 | cyanazine | S-metolachlor + benoxacor |
| I-1 | cyanazine | acetochlor |
| I-1 | cyanazine | acetochlor + dichlormid |
| I-1 | cyanazine | acetochlor + R-29148 |
| I-1 | cyanazine | acetochlor + furilazole |
| I-1 | cyanazine | flufenacet |
| I-2 | amicarbazone | clodinafop-propargyl |
| I-2 | amicarbazone | clodinafop-propargyl + cloquintocet-mexyl |
| I-2 | amicarbazone | fenoxaprop-P-ethyl |
| I-2 | amicarbazone | fenoxaprop-P-ethyl + mefenpyr-diethyl |
| I-2 | amicarbazone | flucarbazone-sodium |
| I-2 | amicarbazone | propoxycarbazone-sodium |
| I-2 | amicarbazone | alachlor |
| I-2 | amicarbazone | dimethenamid |
| I-2 | amicarbazone | S-dimethenamid |
| I-2 | amicarbazone | metolachlor |
| I-2 | amicarbazone | metolachlor + benoxacor |
| I-2 | amicarbazone | S-metolachlor |
| I-2 | amicarbazone | S-metolachlor + benoxacor |
| I-2 | amicarbazone | acetochlor |
| I-2 | amicarbazone | acetochlor + dichlormid |
| I-2 | amicarbazone | acetochlor + R-29148 |
| I-2 | amicarbazone | acetochlor + furilazole |

TABLE 1-continued

| Active compound Group 1 | First active compound of Group 2 | Second active compound of Group 2 (if appropriate + additional active compound of Group 3) |
|---|---|---|
| I-2 | amicarbazone | flufenacet |
| I-2 | atrazine | clodinafop-propargyl |
| I-2 | atrazine | clodinafop-propargyl + cloquintocet-mexyl |
| I-2 | atrazine | fenoxaprop-P-ethyl |
| I-2 | atrazine | fenoxaprop-P-ethyl + mefenpyr-diethyl |
| I-2 | atrazine | flucarbazone-sodium |
| I-2 | atrazine | propoxycarbazone-sodium |
| I-2 | atrazine | alachlor |
| I-2 | atrazine | dimethenamid |
| I-2 | atrazine | S-dimethenamid |
| I-2 | atrazine | metolachlor |
| I-2 | atrazine | metolachlor + benoxacor |
| I-2 | atrazine | S-metolachlor |
| I-2 | atrazine | S-metolachlor + benoxacor |
| I-2 | atrazine | acetochlor |
| I-2 | atrazine | acetochlor + dichlormid |
| I-2 | atrazine | acetochlor + R-29148 |
| I-2 | atrazine | acetochlor + furilazole |
| I-2 | atrazine | flufenacet |
| I-2 | metribuzin | clodinafop-propargyl |
| I-2 | metribuzin | clodinafop-propargyl + cloquintocet-mexyl |
| I-2 | metribuzin | fenoxaprop-P-ethyl |
| I-2 | metribuzin | fenoxaprop-P-ethyl + mefenpyr-diethyl |
| I-2 | metribuzin | flucarbazone-sodium |
| I-2 | metribuzin | propoxycarbazone-sodium |
| I-2 | metribuzin | alachlor |
| I-2 | metribuzin | dimethenamid |
| I-2 | metribuzin | S-dimethenamid |
| I-2 | metribuzin | metolachlor |
| I-2 | metribuzin | metolachlor + benoxacor |
| I-2 | metribuzin | metolachlor |
| I-2 | metribuzin | metolachlor + benoxacor |
| I-2 | metribuzin | acetochlor |
| I-2 | metribuzin | acetochlor + dichlormid |
| I-2 | metribuzin | acetochlor + R-29148 |
| I-2 | metribuzin | acetochlor + furilazole |
| I-2 | metribuzin | flufenacet |
| I-2 | terbuthylazine | clodinafop-propargyl |
| I-2 | terbuthylazine | clodinafop-propargyl + cloquintocet-mexyl |
| I-2 | terbuthylazine | fenoxaprop-P-ethyl |
| I-2 | terbuthylazine | fenoxaprop-P-ethyl + mefenpyr-diethyl |
| I-2 | terbuthylazine | flucarbazone-sodium |
| I-2 | terbuthylazine | propoxycarbazone-sodium |
| I-2 | terbuthylazine | alachlor |
| I-2 | terbuthylazine | dimethenamid |
| I-2 | terbuthylazine | S-dimethenamid |
| I-2 | terbuthylazine | metolachlor |
| I-2 | terbuthylazine | metolachlor + benoxacor |
| I-2 | terbuthylazine | S-metolachlor |
| I-2 | terbuthylazine | S-metolachlor + benoxacor |
| I-2 | terbuthylazine | acetochlor |
| I-2 | terbuthylazine | acetochlor + dichlormid |
| I-2 | terbuthylazine | acetochlor + R-29148 |
| I-2 | terbuthylazine | acetochlor + furilazole |
| I-2 | terbuthylazine | flufenacet |
| I-2 | simazine | clodinafop-propargyl |
| I-2 | simazine | clodinafop-propargyl + cloquintocet-mexyl |
| I-2 | simazine | fenoxaprop-P-ethyl |
| I-2 | simazine | fenoxaprop-P-ethyl + mefenpyr-diethyl |
| I-2 | simazine | flucarbazone-sodium |
| I-2 | simazine | propoxycarbazone-sodium |
| I-2 | simazine | alachlor |
| I-2 | simazine | dimethenamid |
| I-2 | simazine | S-dimethenamid |
| I-2 | simazine | metolachlor |
| I-2 | simazine | metolachlor + benoxacor |
| I-2 | simazine | S-metolachlor |
| I-2 | simazine | S-metolachlor + benoxacor |
| I-2 | simazine | acetochlor |
| I-2 | simazine | acetochlor + dichlormid |
| I-2 | simazine | acetochlor + R-29148 |
| I-2 | simazine | acetochlor + furilazole |
| I-2 | simazine | flufenacet |
| I-2 | cyanazine | clodinafop-propargyl |
| I-2 | cyanazine | clodinafop-propargyl + cloquintocet-mexyl |
| I-2 | cyanazine | fenoxaprop-P-ethyl |
| I-2 | cyanazine | fenoxaprop-P-ethyl + mefenpyr-diethyl |
| I-2 | cyanazine | flucarbazone-sodium |
| I-2 | cyanazine | propoxycarbazone-sodium |
| I-2 | cyanazine | alachlor |
| I-2 | cyanazine | dimethenamid |
| I-2 | cyanazine | S-dimethenamid |
| I-2 | cyanazine | metolachlor |
| I-2 | cyanazine | metolachlor + benoxacor |
| I-2 | cyanazine | S-metolachlor |
| I-2 | cyanazine | S-metolachlor + benoxacor |
| I-2 | cyanazine | acetochlor |
| I-2 | cyanazine | acetochlor + dichlormid |
| I-2 | cyanazine | acetochlor + R-29148 |
| I-2 | cyanazine | acetochlor + furilazole |
| I-2 | cyanazine | flufenacet |
| I-3 | amicarbazone | clodinafop-propargyl |
| I-3 | amicarbazone | clodinafop-propargyl + cloquintocet-mexyl |
| I-3 | amicarbazone | fenoxaprop-P-ethyl |
| I-3 | amicarbazone | fenoxaprop-P-ethyl + mefenpyr-diethyl |
| I-3 | amicarbazone | flucarbazone-sodium |
| I-3 | amicarbazone | propoxycarbazone-sodium |
| I-3 | amicarbazone | alachlor |
| I-3 | amicarbazone | dimethenamid |
| I-3 | amicarbazone | S-dimethenamid |
| I-3 | amicarbazone | metolachlor |
| I-3 | amicarbazone | metolachlor + benoxacor |
| I-3 | amicarbazone | S-metolachlor |
| I-3 | amicarbazone | S-metolachlor + benoxacor |
| I-3 | amicarbazone | acetochlor |
| I-3 | amicarbazone | acetochlor + dichlormid |
| I-3 | amicarbazone | acetochlor + R-29148 |
| I-3 | amicarbazone | acetochlor + furilazole |
| I-3 | amicarbazone | flufenacet |
| I-3 | atrazine | clodinafop-propargyl |
| I-3 | atrazine | clodinafop-propargyl + cloquintocet-mexyl |
| I-3 | atrazine | fenoxaprop-P-ethyl |
| I-3 | atrazine | fenoxaprop-P-ethyl + mefenpyr-diethyl |
| I-3 | atrazine | flucarbazone-sodium |
| I-3 | atrazine | propoxycarbazone-sodium |
| I-3 | atrazine | alachlor |
| I-3 | atrazine | dimethenamid |
| I-3 | atrazine | S-dimethenamid |
| I-3 | atrazine | metolachlor |
| I-3 | atrazine | metolachlor + benoxacor |
| I-3 | atrazine | S-metolachlor |
| I-3 | atrazine | S-metolachlor + benoxacor |
| I-3 | atrazine | acetochlor |
| I-3 | atrazine | acetochlor + dichlormid |
| I-3 | atrazine | acetochlor + R-29148 |
| I-3 | atrazine | acetochlor + furilazole |
| I-3 | atrazine | flufenacet |
| I-3 | metribuzin | clodinafop-propargyl |
| I-3 | metribuzin | clodinafop-propargyl + cloquintocet-mexyl |
| I-3 | metribuzin | fenoxaprop-P-ethyl |
| I-3 | metribuzin | fenoxaprop-P-ethyl + mefenpyr-diethyl |
| I-3 | metribuzin | flucarbazone-sodium |
| I-3 | metribuzin | propoxycarbazone-sodium |
| I-3 | metribuzin | alachlor |
| I-3 | metribuzin | dimethenamid |
| I-3 | metribuzin | S-dimethenamid |
| I-3 | metribuzin | metolachlor |
| I-3 | metribuzin | metolachlor + benoxacor |
| I-3 | metribuzin | metolachlor |
| I-3 | metribuzin | metolachlor + benoxacor |
| I-3 | metribuzin | acetochlor |
| I-3 | metribuzin | acetochlor + dichlormid |

TABLE 1-continued

| Active compound Group 1 | First active compound of Group 2 | Second active compound of Group 2 (if appropriate + additional active compound of Group 3) |
|---|---|---|
| I-3 | metribuzin | acetochlor + R-29148 |
| I-3 | metribuzin | acetochlor + furilazole |
| I-3 | metribuzin | flufenacet |
| I-3 | terbuthylazine | clodinafop-propargyl |
| I-3 | terbuthylazine | clodinafop-propargyl + cloquintocet-mexyl |
| I-3 | terbuthylazine | fenoxaprop-P-ethyl |
| I-3 | terbuthylazine | fenoxaprop-P-ethyl + mefenpyr-diethyl |
| I-3 | terbuthylazine | flucarbazone-sodium |
| I-3 | terbuthylazine | propoxycarbazone-sodium |
| I-3 | terbuthylazine | alachlor |
| I-3 | terbuthylazine | dimethenamid |
| I-3 | terbuthylazine | S-dimethenamid |
| I-3 | terbuthylazine | metolachlor |
| I-3 | terbuthylazine | metolachlor + benoxacor |
| I-3 | terbuthylazine | S-metolachlor |
| I-3 | terbuthylazine | S-metolachlor + benoxacor |
| I-3 | terbuthylazine | acetochlor |
| I-3 | terbuthylazine | acetochlor + dichlormid |
| I-3 | terbuthylazine | acetochlor + R-29148 |
| I-3 | terbuthylazine | flufenacet |
| I-3 | terbuthylazine | acetochlor + furilazole |
| I-3 | simazine | clodinafop-propargyl |
| I-3 | simazine | clodinafop-propargyl + cloquintocet-mexyl |
| I-3 | simazine | fenoxaprop-P-ethyl |
| I-3 | simazine | fenoxaprop-P-ethyl + mefenpyr-diethyl |
| I-3 | simazine | flucarbazone-sodium |
| I-3 | simazine | propoxycarbazone-sodium |
| I-3 | simazine | alachlor |
| I-3 | simazine | dimethenamid |
| I-3 | simazine | S-dimethenamid |
| I-3 | simazine | metolachlor |
| I-3 | simazine | metolachlor + benoxacor |
| I-3 | simazine | S-metolachlor |
| I-3 | simazine | S-metolachlor + benoxacor |
| I-3 | simazine | acetochlor |
| I-3 | simazine | acetochlor + dichlormid |
| I-3 | simazine | acetochlor + R-29148 |
| I-3 | simazine | acetochlor + furilazole |
| I-3 | simazine | flufenacet |
| I-3 | cyanazine | clodinafop-propargyl |
| I-3 | cyanazine | clodinafop-propargyl + cloquintocet-mexyl |
| I-3 | cyanazine | fenoxaprop-P-ethyl |
| I-3 | cyanazine | fenoxaprop-P-ethyl + mefenpyr-diethyl |
| I-3 | cyanazine | flucarbazone-sodium |
| I-3 | cyanazine | propoxycarbazone-sodium |
| I-3 | cyanazine | alachlor |
| I-3 | cyanazine | dimethenamid |
| I-3 | cyanazine | S-dimethenamid |
| I-3 | cyanazine | metolachlor |
| I-3 | cyanazine | metolachlor + benoxacor |
| I-3 | cyanazine | S-metolachlor |
| I-3 | cyanazine | S-metolachlor + benoxacor |
| I-3 | cyanazine | acetochlor |
| I-3 | cyanazine | acetochlor + dichlormid |
| I-3 | cyanazine | acetochlor + R-29148 |
| I-3 | cyanazine | acetochlor + furilazole |
| I-3 | cyanazine | flufenacet |
| I-4 | amicarbazone | clodinafop-propargyl |
| I-4 | amicarbazone | clodinafop-propargyl + cloquintocet-mexyl |
| I-4 | amicarbazone | fenoxaprop-P-ethyl |
| I-4 | amicarbazone | fenoxaprop-P-ethyl + mefenpyr-diethyl |
| I-4 | amicarbazone | flucarbazone-sodium |
| I-4 | amicarbazone | propoxycarbazone-sodium |
| I-4 | amicarbazone | alachlor |
| I-4 | amicarbazone | dimethenamid |
| I-4 | amicarbazone | S-dimethenamid |
| I-4 | amicarbazone | metolachlor |
| I-4 | amicarbazone | metolachlor + benoxacor |
| I-4 | amicarbazone | S-metolachlor |
| I-4 | amicarbazone | S-metolachlor + benoxacor |
| I-4 | amicarbazone | acetochlor |
| I-4 | amicarbazone | acetochlor + dichlormid |
| I-4 | amicarbazone | acetochlor + R-29148 |
| I-4 | amicarbazone | acetochlor + furilazole |
| I-4 | amicarbazone | flufenacet |
| I-4 | atrazine | clodinafop-propargyl |
| I-4 | atrazine | clodinafop-propargyl + cloquintocet-mexyl |
| I-4 | atrazine | fenoxaprop-P-ethyl |
| I-4 | atrazine | fenoxaprop-P-ethyl + mefenpyr-diethyl |
| I-4 | atrazine | flucarbazone-sodium |
| I-4 | atrazine | propoxycarbazone-sodium |
| I-4 | atrazine | alachlor |
| I-4 | atrazine | dimethenamid |
| I-4 | atrazine | S-dimethenamid |
| I-4 | atrazine | metolachlor |
| I-4 | atrazine | metolachlor + benoxacor |
| I-4 | atrazine | S-metolachlor |
| I-4 | atrazine | S-metolachlor + benoxacor |
| I-4 | atrazine | acetochlor |
| I-4 | atrazine | acetochlor + dichlormid |
| I-4 | atrazine | acetochlor + R-29148 |
| I-4 | atrazine | acetochlor + furilazole |
| I-4 | atrazine | flufenacet |
| I-4 | metribuzin | clodinafop-propargyl |
| I-4 | metribuzin | clodinafop-propargyl + cloquintocet-mexyl |
| I-4 | metribuzin | fenoxaprop-P-ethyl |
| I-4 | metribuzin | fenoxaprop-P-ethyl + mefenpyr-diethyl |
| I-4 | metribuzin | flucarbazone-sodium |
| I-4 | metribuzin | propoxycarbazone-sodium |
| I-4 | metribuzin | alachlor |
| I-4 | metribuzin | dimethenamid |
| I-4 | metribuzin | S-dimethenamid |
| I-4 | metribuzin | metolachlor |
| I-4 | metribuzin | metolachlor + benoxacor |
| I-4 | metribuzin | metolachlor |
| I-4 | metribuzin | metolachlor + benoxacor |
| I-4 | metribuzin | acetochlor |
| I-4 | metribuzin | acetochlor + dichlormid |
| I-4 | metribuzin | acetochlor + R-29148 |
| I-4 | metribuzin | acetochlor + furilazole |
| I-4 | metribuzin | flufenacet |
| I-4 | terbuthylazine | clodinafop-propargyl |
| I-4 | terbuthylazine | clodinafop-propargyl + cloquintocet-mexyl |
| I-4 | terbuthylazine | fenoxaprop-P-ethyl |
| I-4 | terbuthylazine | fenoxaprop-P-ethyl + mefenpyr-diethyl |
| I-4 | terbuthylazine | flucarbazone-sodium |
| I-4 | terbuthylazine | propoxycarbazone-sodium |
| I-4 | terbuthylazine | alachlor |
| I-4 | terbuthylazine | dimethenamid |
| I-4 | terbuthylazine | S-dimethenamid |
| I-4 | terbuthylazine | metolachlor |
| I-4 | terbuthylazine | metolachlor + benoxacor |
| I-4 | terbuthylazine | S-metolachlor |
| I-4 | terbuthylazine | S-metolachlor + benoxacor |
| I-4 | terbuthylazine | acetochlor |
| I-4 | terbuthylazine | acetochlor + dichlormid |
| I-4 | terbuthylazine | acetochlor + R-29148 |
| I-4 | terbuthylazine | acetochlor + furilazole |
| I-4 | terbuthylazine | flufenacet |
| I-4 | simazine | clodinafop-propargyl |
| I-4 | simazine | clodinafop-propargyl + cloquintocet-mexyl |
| I-4 | simazine | fenoxaprop-P-ethyl |
| I-4 | simazine | fenoxaprop-P-ethyl + mefenpyr-diethyl |
| I-4 | simazine | flucarbazone-sodium |
| I-4 | simazine | propoxycarbazone-sodium |
| I-4 | simazine | alachlor |
| I-4 | simazine | dimethenamid |
| I-4 | simazine | S-dimethenamid |
| I-4 | simazine | metolachlor |
| I-4 | simazine | metolachlor + benoxacor |
| I-4 | simazine | S-metolachlor |
| I-4 | simazine | S-metolachlor + benoxacor |

TABLE 1-continued

| Active compound Group 1 | First active compound of Group 2 | Second active compound of Group 2 (if appropriate + additional active compound of Group 3) |
|---|---|---|
| I-4 | simazine | acetochlor |
| I-4 | simazine | acetochlor + dichlormid |
| I-4 | simazine | acetochlor + R-29148 |
| I-4 | simazine | acetochlor + furilazole |
| I-4 | simazine | flufenacet |
| I-4 | cyanazine | clodinafop-propargyl |
| I-4 | cyanazine | clodinafop-propargyl + cloquintocet-mexyl |
| I-4 | cyanazine | fenoxaprop-P-ethyl |
| I-4 | cyanazine | fenoxaprop-P-ethyl + mefenpyr-diethyl |
| I-4 | cyanazine | flucarbazone-sodium |
| I-4 | cyanazine | propoxycarbazone-sodium |
| I-4 | cyanazine | alachlor |
| I-4 | cyanazine | dimethenamid |
| I-4 | cyanazine | S-dimethenamid |
| I-4 | cyanazine | metolachlor |
| I-4 | cyanazine | metolachlor + benoxacor |
| I-4 | cyanazine | S-metolachlor |
| I-4 | cyanazine | S-metolachlor + benoxacor |
| I-4 | cyanazine | acetochlor |
| I-4 | cyanazine | acetochlor + dichlormid |
| I-4 | cyanazine | acetochlor + R-29148 |
| I-4 | cyanazine | acetochlor + furilazole |
| I-4 | cyanazine | flufenacet |
| I-5 | amicarbazone | clodinafop-propargyl |
| I-5 | amicarbazone | clodinafop-propargyl + cloquintocet-mexyl |
| I-5 | amicarbazone | fenoxaprop-P-ethyl |
| I-5 | amicarbazone | fenoxaprop-P-ethyl + mefenpyr-diethyl |
| I-5 | amicarbazone | flucarbazone-sodium |
| I-5 | amicarbazone | propoxycarbazone-sodium |
| I-5 | amicarbazone | alachlor |
| I-5 | amicarbazone | dimethenamid |
| I-5 | amicarbazone | S-dimethenamid |
| I-5 | amicarbazone | metolachlor |
| I-5 | amicarbazone | metolachlor + benoxacor |
| I-5 | amicarbazone | S-metolachlor |
| I-5 | amicarbazone | S-metolachlor + benoxacor |
| I-5 | amicarbazone | acetochlor |
| I-5 | amicarbazone | acetochlor + dichlormid |
| I-5 | amicarbazone | acetochlor + R-29148 |
| I-5 | amicarbazone | acetochlor + furilazole |
| I-5 | amicarbazone | flufenacet |
| I-5 | atrazine | clodinafop-propargyl |
| I-5 | atrazine | clodinafop-propargyl + cloquintocet-mexyl |
| I-5 | atrazine | fenoxaprop-P-ethyl |
| I-5 | atrazine | fenoxaprop-P-ethyl + mefenpyr-diethyl |
| I-5 | atrazine | flucarbazone-sodium |
| I-5 | atrazine | propoxycarbazone-sodium |
| I-5 | atrazine | alachlor |
| I-5 | atrazine | dimethenamid |
| I-5 | atrazine | S-dimethenamid |
| I-5 | atrazine | metolachlor |
| I-5 | atrazine | metolachlor + benoxacor |
| I-5 | atrazine | S-metolachlor |
| I-5 | atrazine | S-metolachlor + benoxacor |
| I-5 | atrazine | acetochlor |
| I-5 | atrazine | acetochlor + dichlormid |
| I-5 | atrazine | acetochlor + R-29148 |
| I-5 | atrazine | acetochlor + furilazole |
| I-5 | atrazine | flufenacet |
| I-5 | metribuzin | clodinafop-propargyl |
| I-5 | metribuzin | clodinafop-propargyl + cloquintocet-mexyl |
| I-5 | metribuzin | fenoxaprop-P-ethyl |
| I-5 | metribuzin | fenoxaprop-P-ethyl + mefenpyr-diethyl |
| I-5 | metribuzin | flucarbazone-sodium |
| I-5 | metribuzin | propoxycarbazone-sodium |
| I-5 | metribuzin | alachlor |
| I-5 | metribuzin | dimethenamid |
| I-5 | metribuzin | S-dimethenamid |
| I-5 | metribuzin | metolachlor |
| I-5 | metribuzin | metolachlor + benoxacor |
| I-5 | metribuzin | metolachlor |
| I-5 | metribuzin | metolachlor + benoxacor |
| I-5 | metribuzin | acetochlor |
| I-5 | metribuzin | acetochlor + dichlormid |
| I-5 | metribuzin | acetochlor + R-29148 |
| I-5 | metribuzin | acetochlor + furilazole |
| I-5 | metribuzin | flufenacet |
| I-5 | terbuthylazine | clodinafop-propargyl |
| I-5 | terbuthylazine | clodinafop-propargyl + cloquintocet-mexyl |
| I-5 | terbuthylazine | fenoxaprop-P-ethyl |
| I-5 | terbuthylazine | fenoxaprop-P-ethyl + mefenpyr-diethyl |
| I-5 | terbuthylazine | flucarbazone-sodium |
| I-5 | terbuthylazine | propoxycarbazone-sodium |
| I-5 | terbuthylazine | alachlor |
| I-5 | terbuthylazine | dimethenamid |
| I-5 | terbuthylazine | S-dimethenamid |
| I-5 | terbuthylazine | metolachlor |
| I-5 | terbuthylazine | metolachlor + benoxacor |
| I-5 | terbuthylazine | S-metolachlor |
| I-5 | terbuthylazine | S-metolachlor + benoxacor |
| I-5 | terbuthylazine | acetochlor |
| I-5 | terbuthylazine | acetochlor + dichlormid |
| I-5 | terbuthylazine | acetochlor + R-29148 |
| I-5 | terbuthylazine | acetochlor + furilazole |
| I-5 | terbuthylazine | flufenacet |
| I-5 | simazine | clodinafop-propargyl |
| I-5 | simazine | clodinafop-propargyl + cloquintocet-mexyl |
| I-5 | simazine | fenoxaprop-P-ethyl |
| I-5 | simazine | fenoxaprop-P-ethyl + mefenpyr-diethyl |
| I-5 | simazine | flucarbazone-sodium |
| I-5 | simazine | propoxycarbazone-sodium |
| I-5 | simazine | alachlor |
| I-5 | simazine | dimethenamid |
| I-5 | simazine | S-dimethenamid |
| I-5 | simazine | metolachlor |
| I-5 | simazine | metolachlor + benoxacor |
| I-5 | simazine | S-metolachlor |
| I-5 | simazine | S-metolachlor + benoxacor |
| I-5 | simazine | acetochlor |
| I-5 | simazine | acetochlor + dichlormid |
| I-5 | simazine | acetochlor + R-29148 |
| I-5 | simazine | acetochlor + furilazole |
| I-5 | simazine | flufenacet |
| I-5 | cyanazine | clodinafop-propargyl |
| I-5 | cyanazine | clodinafop-propargyl + cloquintocet-mexyl |
| I-5 | cyanazine | fenoxaprop-P-ethyl |
| I-5 | cyanazine | fenoxaprop-P-ethyl + mefenpyr-diethyl |
| I-5 | cyanazine | flucarbazone-sodium |
| I-5 | cyanazine | propoxycarbazone-sodium |
| I-5 | cyanazine | alachlor |
| I-5 | cyanazine | dimethenamid |
| I-5 | cyanazine | S-dimethenamid |
| I-5 | cyanazine | metolachlor |
| I-5 | cyanazine | metolachlor + benoxacor |
| I-5 | cyanazine | S-metolachlor |
| I-5 | cyanazine | S-metolachlor + benoxacor |
| I-5 | cyanazine | acetochlor |
| I-5 | cyanazine | acetochlor + dichlormid |
| I-5 | cyanazine | acetochlor + R-29148 |
| I-5 | cyanazine | acetochlor + furilazole |
| I-5 | cyanazine | flufenacet |
| I-6 | amicarbazone | clodinafop-propargyl |
| I-6 | amicarbazone | clodinafop-propargyl + cloquintocet-mexyl |
| I-6 | amicarbazone | fenoxaprop-P-ethyl |
| I-6 | amicarbazone | fenoxaprop-P-ethyl + mefenpyr-diethyl |
| I-6 | amicarbazone | flucarbazone-sodium |
| I-6 | amicarbazone | propoxycarbazone-sodium |
| I-6 | amicarbazone | alachlor |
| I-6 | amicarbazone | dimethenamid |
| I-6 | amicarbazone | S-dimethenamid |
| I-6 | amicarbazone | metolachlor |
| I-6 | amicarbazone | metolachlor + benoxacor |

TABLE 1-continued

| Active compound Group 1 | First active compound of Group 2 | Second active compound of Group 2 (if appropriate + additional active compound of Group 3) |
|---|---|---|
| I-6 | amicarbazone | S-metolachlor |
| I-6 | amicarbazone | S-metolachlor + benoxacor |
| I-6 | amicarbazone | acetochlor |
| I-6 | amicarbazone | acetochlor + dichlormid |
| I-6 | amicarbazone | acetochlor + R-29148 |
| I-6 | amicarbazone | acetochlor + furilazole |
| I-6 | amicarbazone | flufenacet |
| I-6 | atrazine | clodinafop-propargyl |
| I-6 | atrazine | clodinafop-propargyl + cloquintocet-mexyl |
| I-6 | atrazine | fenoxaprop-P-ethyl |
| I-6 | atrazine | fenoxaprop-P-ethyl + mefenpyr-diethyl |
| I-6 | atrazine | flucarbazone-sodium |
| I-6 | atrazine | propoxycarbazone-sodium |
| I-6 | atrazine | alachlor |
| I-6 | atrazine | dimethenamid |
| I-6 | atrazine | S-dimethenamid |
| I-6 | atrazine | metolachlor |
| I-6 | atrazine | metolachlor + benoxacor |
| I-6 | atrazine | S-metolachlor |
| I-6 | atrazine | S-metolachlor + benoxacor |
| I-6 | atrazine | acetochlor |
| I-6 | atrazine | acetochlor + dichlormid |
| I-6 | atrazine | acetochlor + R-29148 |
| I-6 | atrazine | acetochlor + furilazole |
| I-6 | atrazine | flufenacet |
| I-6 | metribuzin | clodinafop-propargyl |
| I-6 | metribuzin | clodinafop-propargyl + cloquintocet-mexyl |
| I-6 | metribuzin | fenoxaprop-P-ethyl |
| I-6 | metribuzin | fenoxaprop-P-ethyl + mefenpyr-diethyl |
| I-6 | metribuzin | flucarbazone-sodium |
| I-6 | metribuzin | propoxycarbazone-sodium |
| I-6 | metribuzin | alachlor |
| I-6 | metribuzin | dimethenamid |
| I-6 | metribuzin | S-dimethenamid |
| I-6 | metribuzin | metolachlor |
| I-6 | metribuzin | metolachlor + benoxacor |
| I-6 | metribuzin | metolachlor |
| I-6 | metribuzin | metolachlor + benoxacor |
| I-6 | metribuzin | acetochlor |
| I-6 | metribuzin | acetochlor + dichlormid |
| I-6 | metribuzin | acetochlor + R-29148 |
| I-6 | metribuzin | acetochlor + furilazole |
| I-6 | metribuzin | flufenacet |
| I-6 | terbuthylazine | clodinafop-propargyl |
| I-6 | terbuthylazine | clodinafop-propargyl + cloquintocet-mexyl |
| I-6 | terbuthylazine | fenoxaprop-P-ethyl |
| I-6 | terbuthylazine | fenoxaprop-P-ethyl + mefenpyr-diethyl |
| I-6 | terbuthylazine | flucarbazone-sodium |
| I-6 | terbuthylazine | propoxycarbazone-sodium |
| I-6 | terbuthylazine | alachlor |
| I-6 | terbuthylazine | dimethenamid |
| I-6 | terbuthylazine | S-dimethenamid |
| I-6 | terbuthylazine | metolachlor |
| I-6 | terbuthylazine | metolachlor + benoxacor |
| I-6 | terbuthylazine | S-metolachlor |
| I-6 | terbuthylazine | S-metolachlor + benoxacor |
| I-6 | terbuthylazine | acetochlor |
| I-6 | terbuthylazine | acetochlor + dichlormid |
| I-6 | terbuthylazine | acetochlor + R-29148 |
| I-6 | terbuthylazine | acetochlor + furilazole |
| I-6 | terbuthylazine | flufenacet |
| I-6 | simazine | clodinafop-propargyl |
| I-6 | simazine | clodinafop-propargyl + cloquintocet-mexyl |
| I-6 | simazine | fenoxaprop-P-ethyl |
| I-6 | simazine | fenoxaprop-P-ethyl + mefenpyr-diethyl |
| I-6 | simazine | flucarbazone-sodium |
| I-6 | simazine | propoxycarbazone-sodium |
| I-6 | simazine | alachlor |
| I-6 | simazine | dimethenamid |
| I-6 | simazine | S-dimethenamid |
| I-6 | simazine | metolachlor |
| I-6 | simazine | metolachlor + benoxacor |
| I-6 | simazine | S-metolachlor |
| I-6 | simazine | S-metolachlor + benoxacor |
| I-6 | simazine | acetochlor |
| I-6 | simazine | acetochlor + dichlormid |
| I-6 | simazine | acetochlor + R-29148 |
| I-6 | simazine | acetochlor + furilazole |
| I-6 | simazine | flufenacet |
| I-6 | cyanazine | clodinafop-propargyl |
| I-6 | cyanazine | clodinafop-propargyl + cloquintocet-mexyl |
| I-6 | cyanazine | fenoxaprop-P-ethyl |
| I-6 | cyanazine | fenoxaprop-P-ethyl + mefenpyr-diethyl |
| I-6 | cyanazine | flucarbazone-sodium |
| I-6 | cyanazine | propoxycarbazone-sodium |
| I-6 | cyanazine | alachlor |
| I-6 | cyanazine | dimethenamid |
| I-6 | cyanazine | S-dimethenamid |
| I-6 | cyanazine | metolachlor |
| I-6 | cyanazine | metolachlor + benoxacor |
| I-6 | cyanazine | S-metolachlor |
| I-6 | cyanazine | S-metolachlor + benoxacor |
| I-6 | cyanazine | acetochlor |
| I-6 | cyanazine | acetochlor + dichlormid |
| I-6 | cyanazine | acetochlor + R-29148 |
| I-6 | cyanazine | acetochlor + furilazole |
| I-6 | cyanazine | flufenacet |

Further examples of combinations according to the invention comprising in each case one active compound of Group 1 and one or two active compounds of Group 2 and/or one active compound of Group 3 are listed in Table 2 below.

TABLE 2

| Active compound of Group 1 | Compounds of Group 2 and/or 3 |
|---|---|
| I-1 | acetochlor |
| I-1 | acetochlor + dichlormid |
| I-1 | acetochlor + R-29148 |
| I-1 | acetochlor + furilazole |
| I-1 | alachlor |
| I-1 | amicarbazone |
| I-1 | amitrole |
| I-1 | atrazine |
| I-1 | bromacil |
| I-1 | carfentrazone-ethyl |
| I-1 | chlorimuron-ethyl |
| I-1 | cyanazine |
| I-1 | diclosulam |
| I-1 | dimethenamid |
| I-1 | S-dimethenamid |
| I-1 | diuron |
| I-1 | EPTC |
| I-1 | fentrazamide |
| I-1 | flucarbazone-sodium |
| I-1 | flufenacet |
| I-1 | flumetsulam |
| I-1 | glufosinate-ammonium |
| I-1 | glyphosate-isopropylammonium |
| I-1 | imazamox |
| I-1 | imazaquin |
| I-1 | imazamethapyr |
| I-1 | isoxaflutole |
| I-1 | mesotrione |
| I-1 | metolachlor |
| I-1 | metolachlor + benoxacor |
| I-1 | S-metolachlor |
| I-1 | S-metolachlor + benoxacor |
| I-1 | metosulam |
| I-1 | metribuzin |

TABLE 2-continued

| Active compound of Group 1 | Compounds of Group 2 and/or 3 |
|---|---|
| I-1 | nicosulfuron |
| I-1 | norflurazon |
| I-1 | pendimethalin |
| I-1 | propoxycarbazone-sodium |
| I-1 | rimsulfuron |
| I-1 | simazin |
| I-1 | sulcotrione |
| I-1 | sulfentrazone |
| I-1 | sulfometuron-methyl |
| I-1 | sulfosate |
| I-1 | terbuthylazine |
| I-1 | thifensulfuron-methyl |
| I-1 | trifluralin |
| I-1 | clodinafop-propargyl |
| I-1 | clodinafop-propargyl + cloquintocet-mexyl |
| I-1 | fenoxaprop-P-ethyl |
| I-1 | fenoxaprop-P-ethyl + mefenpyr-diethyl |
| I-1 | flufenacet + diflufenican |
| I-1 | flufenacet + isoxaflutole |
| I-1 | flufenacet + metosulam |
| I-1 | bromacil + diuron |
| I-2 | acetochlor |
| I-2 | acetochlor + dichlormid |
| I-2 | acetochlor + R-29148 |
| I-2 | acetochlor + furilazole |
| I-2 | alachlor |
| I-2 | amicarbazone |
| I-2 | amitrole |
| I-2 | atrazine |
| I-2 | bromacil |
| I-2 | carfentrazone-ethyl |
| I-2 | chlorimuron-ethyl |
| I-2 | cyanazine |
| I-2 | diclosulam |
| I-2 | dimethenamid |
| I-2 | S-dimethenamid |
| I-2 | diuron |
| I-2 | EPTC |
| I-2 | fentrazamide |
| I-2 | flucarbazone-sodium |
| I-2 | flufenacet |
| I-2 | flumetsulam |
| I-2 | glufosinate-ammonium |
| I-2 | glyphosate-isopropylammonium |
| I-2 | imazamox |
| I-2 | imazaquin |
| I-2 | imazamethapyr |
| I-2 | isoxaflutole |
| I-2 | mesotrione |
| I-2 | metolachlor |
| I-2 | metolachlor + benoxacor |
| I-2 | S-metolachlor |
| I-2 | S-metolachlor + benoxacor |
| I-2 | metosulam |
| I-2 | metribuzin |
| I-2 | nicosulfuron |
| I-2 | norflurazon |
| I-2 | pendimethalin |
| I-2 | propoxycarbazone-sodium |
| I-2 | rimsulfuron |
| I-2 | simazin |
| I-2 | sulcotrione |
| I-2 | sulfentrazone |
| I-2 | sulfometuron-methyl |
| I-2 | sulfosate |
| I-2 | terbuthylazine |
| I-2 | thifensulfuron-methyl |
| I-2 | trifluralin |
| I-2 | clodinafop-propargyl |
| I-2 | clodinafop-propargyl + cloquintocet-mexyl |
| I-2 | fenoxaprop-P-ethyl |
| I-2 | fenoxaprop-P-ethyl + mefenpyr-diethyl |
| I-2 | flufenacet + diflufenican |
| I-2 | flufenacet + isoxaflutole |
| I-2 | flufenacet + metosulam |
| I-2 | bromacil + diuron |
| I-3 | acetochlor |
| I-3 | acetochlor + dichlormid |
| I-3 | acetochlor + R-29148 |
| I-3 | acetochlor + furilazole |
| I-3 | alachlor |
| I-3 | amicarbazone |
| I-3 | amitrole |
| I-3 | atrazine |
| I-3 | bromacil |
| I-3 | carfentrazone-ethyl |
| I-3 | chlorimuron-ethyl |
| I-3 | cyanazine |
| I-3 | diclosulam |
| I-3 | dimethenamid |
| I-3 | S-dimethenamid |
| I-3 | diuron |
| I-3 | EPTC |
| I-3 | fentrazamide |
| I-3 | flucarbazone-sodium |
| I-3 | flufenacet |
| I-3 | flumetsulam |
| I-3 | glufosinate-ammonium |
| I-3 | glyphosate-isopropylammonium |
| I-3 | imazamox |
| I-3 | imazaquin |
| I-3 | imazamethapyr |
| I-3 | isoxaflutole |
| I-3 | mesotrione |
| I-3 | metolachlor |
| I-3 | metolachlor + benoxacor |
| I-3 | S-metolachlor |
| I-3 | S-metolachlor + benoxacor |
| I-3 | metosulam |
| I-3 | metribuzin |
| I-3 | nicosulfuron |
| I-3 | norflurazon |
| I-3 | pendimethalin |
| I-3 | propoxycarbazone-sodium |
| I-3 | rimsulfuron |
| I-3 | simazin |
| I-3 | sulcotrione |
| I-3 | sulfentrazone |
| I-3 | sulfometuron-methyl |
| I-3 | sulfosate |
| I-3 | terbuthylazine |
| I-3 | thifensulfuron-methyl |
| I-3 | trifluralin |
| I-3 | clodinafop-propargyl |
| I-3 | clodinafop-propargyl + cloquintocet-mexyl |
| I-3 | fenoxaprop-P-ethyl |
| I-3 | fenoxaprop-P-ethyl + mefenpyr-diethyl |
| I-3 | flufenacet + diflufenican |
| I-3 | flufenacet + isoxaflutole |
| I-3 | flufenacet + metosulam |
| I-3 | bromacil + diuron |
| I-4 | acetochlor |
| I-4 | acetochlor + dichlormid |
| I-4 | acetochlor + R-29148 |
| I-4 | acetochlor + furilazole |
| I-4 | alachlor |
| I-4 | amicarbazone |
| I-4 | amitrole |
| I-4 | atrazine |
| I-4 | bromacil |
| I-4 | carfentrazone-ethyl |
| I-4 | chlorimuron-ethyl |
| I-4 | cyanazine |
| I-4 | diclosulam |
| I-4 | dimethenamid |
| I-4 | S-dimethenamid |
| I-4 | diuron |
| I-4 | EPTC |
| I-4 | fentrazamide |
| I-4 | flucarbazone-sodium |
| I-4 | flufenacet |
| I-4 | flumetsulam |

TABLE 2-continued

| Active compound of Group 1 | Compounds of Group 2 and/or 3 |
|---|---|
| I-4 | glufosinate-ammonium |
| I-4 | glyphosate-isopropylammonium |
| I-4 | imazamox |
| I-4 | imazaquin |
| I-4 | imazamethapyr |
| I-4 | isoxaflutole |
| I-4 | mesotrione |
| I-4 | metolachlor |
| I-4 | metolachlor + benoxacor |
| I-4 | S-metolachlor |
| I-4 | S-metolachlor + benoxacor |
| I-4 | metosulam |
| I-4 | metribuzin |
| I-4 | nicosulfuron |
| I-4 | norflurazon |
| I-4 | pendimethalin |
| I-4 | propoxycarbazone-sodium |
| I-4 | rimsulfuron |
| I-4 | simazin |
| I-4 | sulcotrione |
| I-4 | sulfentrazone |
| I-4 | sulfometuron-methyl |
| I-4 | sulfosate |
| I-4 | terbuthylazine |
| I-4 | thifensulfuron-methyl |
| I-4 | trifluralin |
| I-4 | clodinafop-propargyl |
| I-4 | clodinafop-propargyl + cloquintocet-mexyl |
| I-4 | fenoxaprop-P-ethyl |
| I-4 | fenoxaprop-P-ethyl + mefenpyr-diethyl |
| I-4 | flufenacet + diflufenican |
| I-4 | flufenacet + isoxaflutole |
| I-4 | flufenacet + metosulam |
| I-4 | bromacil + diuron |
| I-5 | acetochlor |
| I-5 | acetochlor + dichlormid |
| I-5 | acetochlor + R-29148 |
| I-5 | acetochlor + furilazole |
| I-5 | alachlor |
| I-5 | amicarbazone |
| I-5 | amitrole |
| I-5 | atrazine |
| I-5 | bromacil |
| I-5 | carfentrazone-ethyl |
| I-5 | chlorimuron-ethyl |
| I-5 | cyanazine |
| I-5 | diclosulam |
| I-5 | dimethenamid |
| I-5 | S-dimethenamid |
| I-5 | diuron |
| I-5 | EPTC |
| I-5 | fentrazamide |
| I-5 | flucarbazone-sodium |
| I-5 | flufenacet |
| I-5 | flumetsulam |
| I-5 | glufosinate-ammonium |
| I-5 | glyphosate-isopropylammonium |
| I-5 | imazamox |
| I-5 | imazaquin |
| I-5 | imazamethapyr |
| I-5 | isoxaflutole |
| I-5 | mesotrione |
| I-5 | metolachlor |
| I-5 | metolachlor + benoxacor |
| I-5 | S-metolachlor |
| I-5 | S-metolachlor + benoxacor |
| I-5 | metosulam |
| I-5 | metribuzin |
| I-5 | nicosulfuron |
| I-5 | norflurazon |
| I-5 | pendimethalin |
| I-5 | propoxycarbazone-sodium |
| I-5 | rimsulfuron |
| I-5 | simazin |
| I-5 | sulcotrione |
| I-5 | sulfentrazone |
| I-5 | sulfometuron-methyl |
| I-5 | sulfosate |
| I-5 | terbuthylazine |
| I-5 | thifensulfuron-methyl |
| I-5 | trifluralin |
| I-5 | clodinafop-propargyl |
| I-5 | clodinafop-propargyl + cloquintocet-mexyl |
| I-5 | fenoxaprop-P-ethyl |
| I-5 | fenoxaprop-P-ethyl + mefenpyr-diethyl |
| I-5 | flufenacet + diflufenican |
| I-5 | flufenacet + isoxaflutole |
| I-5 | flufenacet + metosulam |
| I-5 | bromacil + diuron |
| I-6 | acetochlor |
| I-6 | acetochlor + dichlormid |
| I-6 | acetochlor + R-29148 |
| I-6 | acetochlor + furilazole |
| I-6 | alachlor |
| I-6 | amicarbazone |
| I-6 | amitrole |
| I-6 | atrazine |
| I-6 | bromacil |
| I-6 | carfentrazone-ethyl |
| I-6 | chlorimuron-ethyl |
| I-6 | cyanazine |
| I-6 | diclosulam |
| I-6 | dimethenamid |
| I-6 | S-dimethenamid |
| I-6 | diuron |
| I-6 | EPTC |
| I-6 | fentrazamide |
| I-6 | flucarbazone-sodium |
| I-6 | flufenacet |
| I-6 | flumetsulam |
| I-6 | glufosinate-ammonium |
| I-6 | glyphosate-isopropylammonium |
| I-6 | imazamox |
| I-6 | imazaquin |
| I-6 | imazamethapyr |
| I-6 | isoxaflutole |
| I-6 | mesotrione |
| I-6 | metolachlor |
| I-6 | metolachlor + benoxacor |
| I-6 | S-metolachlor |
| I-6 | S-metolachlor + benoxacor |
| I-6 | metosulam |
| I-6 | metribuzin |
| I-6 | nicosulfuron |
| I-6 | norflurazon |
| I-6 | pendimethalin |
| I-6 | propoxycarbazone-sodium |
| I-6 | rimsulfuron |
| I-6 | simazin |
| I-6 | sulcotrione |
| I-6 | sulfentrazone |
| I-6 | sulfometuron-methyl |
| I-6 | sulfosate |
| I-6 | terbuthylazine |
| I-6 | thifensulfuron-methyl |
| I-6 | trifluralin |
| I-6 | clodinafop-propargyl |
| I-6 | clodinafop-propargyl + cloquintocet |
| I-6 | fenoxaprop-P-ethyl |
| I-6 | fenoxaprop-P-ethyl + mefenpyr-diethyl |
| I-6 | flufenacet + diflufenican |
| I-6 | flufenacet + isoxaflutole |
| I-6 | flufenacet + metosulam |
| I-6 | bromacil + diuron |

Surprisingly, it has now been found that the above-defined active compound combinations of the N-Aryl-uracils of the formula (I) and the abovementioned active compounds of Group 2 exhibit a particularly high herbicidal activity combined with very good crop plant compatibility and can be used for the selective control of monocotyledonous and dicotyledonous weeds in a variety of crops, in particular in cereals, such as, for example, wheat, barley or oats, and maize, and additionally also for controlling monocotyledonous and dicotyledonous weeds in the semi- and non-selective field. This effect is particularly pronounced in cereals. Likewise, the effect is particularly pronounced in maize.

Surprisingly, the herbicidal activity of the active compound combinations according to the invention of compounds of the abovementioned Groups 1 and 2 exceeds the total of the action of the individual active compounds considerably.

Thus, not just a complementation of actions but a synergistic effect is present which could not have been predicted. The new active compound combinations are well tolerated in a variety of crops, also effecting good control of weeds which are usually difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges. In general, from 0.01 to 1000 parts by weight, preferably from 0.02 to 500 parts by weight and particularly preferably from 0.05 to 100 parts by weight of active compound of Group 2 are used per part by weight of active compound of the formula (I).

The following may be particularly emphasized as mixing components from amongst the active compounds of Group 3:

1-methyl-hexyl 5-chloro-quinoxalin-8-oxy-acetate (cloquintocet-mexyl), ethyl 4,5-dihydro-5,5-diphenyl-3-isoxazolecarboxylate (isoxadifen-ethyl) and diethyl 1-(2,4-dichloro-phenyl)-4,5-dihydro-5-methyl-1H-pyrazole-3,5-dicarboxylate (mefenpyrdiethyl), which are particularly suitable for improving the compatibility in cereals, and 4-dichloroacetyl-1-oxa-4-aza-spiro [4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 2,2-dichloro-N,N-di-2-propenyl-acetamide (dichlormid), 3-dichloroacetyl-5-(2-furanyl)-2,2-dimethyloxazolidine (furilazole, MON-13900) and 3-dichloroacetyl-2,2,5-trimethyl-oxazolidine (R-29148), which are particularly suitable for improving the compatibility in maize.

It must be considered as surprising that, from amongst a multiplicity of known safeners or antidotes capable of antagonizing the harmful effects of a herbicide on the crop plants, it is precisely the abovementioned compounds of Group 3 which are capable of almost completely compensating the harmful effect, on the crop plants, of active compounds of the formula (I) and their salts, if appropriate also in combination with one or more of the abovementioned active compounds of Group 2, without adversely affecting the herbicidal efficacy towards the weeds.

Surprisingly, it has also been found that the herbicidally active substance 2,4-dichlorophenoxy-acetic acid (2,4-D) and its derivatives, too, can play the safener role described above.

Accordingly, a preferred embodiment is also a mixture comprising a compound of the formula (I) and/or salts thereof on the one hand, and 2,4-D and/or its derivatives on the other hand, if appropriate in combination with one or more of the active compounds of Group 2 listed above. Typical derivatives of 2,4-D are, for example, its esters.

Surprisingly, it has also been found that the herbicidally active substances (4-chloro-2-methylphenoxy)acetic acid (MCPA) and (+-)-2-(4-chloro-2-methylphenoxy)propanoic acid (mecoprop) can also play a safener role. The compounds mentioned are described in the following patent applications: JP 63 072 605 und GB 00 820 180.

The compounds diethyl 1-(2,4-dichlorophenyl)-4,5-dihydro-5-methyl-1H-pyrazole-3,5-dicarboxylate (mefenpyr-diethyl), 1-methyl-hexyl [(5-chloro-8-quinolinyl)oxy]acetate (cloquintocet-mexyl) and ethyl 1-(2,4-dichlorophenyl)-5-(trichloromethyl)-1H-1,2,4-triazole-3-carboxylate (fenchlorazole-ethyl) are described in the following patent applications: DE-A-39 39 503, EP-A-191 736 and DE-A-35 25 205. 2,4-D is a known herbicide.

The advantageous effect of the crop plant compatibility of the active compound combinations according to the invention is likewise particularly strongly pronounced at certain concentration ratios. However, the weight ratios of the active compounds in the active compound combinations can be varied within relatively wide ranges. In general, from 0.001 to 1000 parts by weight, preferably from 0.01 to 100 parts by weight and particularly preferably from 0.1 to 10 parts by weight of one of the crop plant compatibility-improving compounds mentioned above under (c) (antidotes/safeners) are used per part by weight of active compound of the formula (I).

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, is, flowers, fruiting bodies, fruits, seeds, roots, tubers and rhizomes. The plant parts also include vegetative and generative propagation material, for example cuttings, tubers, rhizomes, seedlings and seeds.

The treatment according to the invention of the plant and plant parts with the active compounds is carried out directly or by allowing the compounds to act on the surroundings, environment or storage space by the customary treatmnent methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized are those which tolerate so-called ALS, 4-HPPD, EPSP and/or PPO inhibitors, such as, for example, Acuron plants.

The active compounds according to the invention can be used, for example, in the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compound combinations according to the invention is in no way restricted to these genera, but also extends in the same manner to other plants.

The active compound combinations to be used in accordance with the invention can be employed not only in conventional cultivation methods (suitably spaced row crops), in plantation crops (for example grapevines, fruit, citrus) and in industrial plants and railtracks, on paths and squares, but also for stubble treatment and in the minimum tillage method. They are furthermore suitable as dessicants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

In the case of the use of water as an extender, organic solvents can, for example, also be used as cosolvents. The following are essentially suitable as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are:

for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The new active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellants, growth substances, plant nutrients and soil conditioners is also possible. It may furthermore be advantageous for specific applications, in particular for the post-emergence method, to incorporate into the formulations plant-tolerated mineral or vegetable oils (for example the commercial product "Rako Binol") or ammonium salts such as, for example, ammonium sulphate or ammonium thiocyanate, as further additives.

The new active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say by the pre- and post-emergence method. They may also be incorporated into the soil prior to sowing.

The good herbicidal action of the new active compound combinations can be seen from the examples which follow. While the individual active compounds show weaknesses with regard to their herbicidal action, the combinations all show a very good herbicidal action which exceeds a simple sum of actions.

A synergistic effect in herbicides is always present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, Pages 20–22, 1967):

If
$X =$ % damage by herbicide A (active compound of the formula I) at an application rate of p kg/ha
and
$Y =$ % damage by herbicide B (active compound of the formula II) at an application rate of q kg/ha
and
$E =$ the expected damage of herbicides A + B at an application rate of p + q kg/ha,
then
$E = X + Y - (X * Y/100)$.

If the actual damage exceeds the calculated value, the combination has a superadditive effect, that is to say a synergistic effect.

The theoretically expected activity for a given combination of three herbicides can likewise be found in the literature mentioned above.

USE EXAMPLES

Example A

Pre-emergence-test

Solvent: 2 to 3 parts by weight of acetone or N,N-dimethyl-formamide

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration. Formulated products are dissolved in water and then diluted with water to the desired concentration.

The solutions of the other mixing components (active compounds or safeners) are prepared analogously. The separately prepared solutions of the various mixing components are then combined and, if appropriate, additional substances (formulation auxiliaries, additives, etc.) are added and, if appropriate, water is added to prepare the desired dilution.

Seeds of the test plants are sown in standard soil. After 24 hours, the soil is sprayed with the preparation of active compound such that the particular amount of active compound desired in each case is applied per unit area. The concentration of active compound in the spray liquor is chosen such that the particular amount of active compound desired in each case is applied in 500 litres of water per hectare. The containers with the test plants are kept in a greenhouse at controlled temperature and controlled illumination until evaluation.

After three weeks, the degree of damage to the plants is rated in % damage in comparison to the development of the untreated control. The figures denote 0%=no effect/no damage (like untreated control)

100%=total destruction

In this test, for example, combinations of the compound (I-3) with the compounds 4-dichloroacetyl-1-oxa-4-aza-spiro[4.5]-decane (AD-67) and phenylmethyl 2-chloro-4-trifluoromethyl-thiazole-5-carboxylate (flurazole) show considerably better compatibility with crop plants, such as, for example, maize, than the compound (I-3) on its own (cf. Table A1).

TABLE A1

Pre-emergence test in maize

| Active compound 1 | Application rate (g of a.i./ha) | Active compound 2 | Application rate (g of a.i./ha) | Number of maize plants | Average damage (%) |
|---|---|---|---|---|---|
| I-3 | 90 | | | 48 | 36 |
| I-3 | 60 | | | 44 | 17 |
| I-3 | 90 | AD-67 | 500 | 45 | 21 |
| I-3 | 60 | AD-67 | 500 | 47 | 10 |
| I-3 | 90 | AD-67 | 60 | 42 | 20 |
| I-3 | 60 | AD-67 | 60 | 39 | 18 |
| I-3 | 90 | AD-67 | 30 | 47 | 21 |
| I-3 | 60 | AD-67 | 30 | 47 | 14 |
| I-3 | 90 | flurazole | 500 | 48 | 18 |
| I-3 | 60 | flurazole | 500 | 47 | 8 |
| I-3 | 90 | flurazole | 60 | 48 | 27 |
| I-3 | 60 | flurazole | 60 | 46 | 10 |
| I-3 | 90 | flurazole | 30 | 33 | 36 |
| I-3 | 60 | flurazole | 30 | 43 | 16 |

All variants were treated with 0.1% Renex-36 in the spray liquor.

Furthermore, in this test combinations of the compound (I-6) with the compound diethyl 1-(2,4-dichlorophenyl)-4,5-dihydro-5-methyl-1H-pyrazole-3,5-dicarboxylate (mefenpyr-diethyl) show considerably better compatibility with crop plants, such as, for example, barley and wheat, than the compound (I-6) on its own (cf. Table A2).

TABLE A2

Post-emergence test in barley and wheat

| Active compounds | Application rates (g of a.i./ha) | Winter barley (21 days) | Summer wheat (21 days) | Durum wheat (5 days) | Winter wheat (21 days) | Summer wheat (5 days) | Summer wheat (22 days) | Durum wheat (22 days) |
|---|---|---|---|---|---|---|---|---|
| (I-6) | 30 | 30 | 30 | 30 | — | 60 | 30 | 20 |
| (I-6) | 15 | 20 | 20 | 20 | 10 | 50 | 20 | — |
| (I-6) + mefenpyr-diethyl | 30 + 30 | 20 | 20 | 20 | — | 50 | 20 | 10 |
| (I-6) + mefenpyr-diethyl | 15 + 15 | 10 | 10 | 10 | 5 | 40 | 10 | — |

All variants were treated with 0.1% Renex-36 in the spray liquor.

Furthermore, in this test combinations of the compound (I-6) with the compounds 1-methylhexyl 5-chloro-quinoxalin-8-oxy-acetate (cloquintocet-mexyl) and ethyl 1-(2,4-dichloro-phenyl)-5-trichloromethyl-1H-1,2,4-triazole-3-carboxylate (fenchlorazol-ethyl) show considerably better compatibility with crop plants, such as, for example, barley and wheat, than the compound (I-6) on its own (cf. Table A3).

TABLE A3

Post-emergence test in barley and wheat

| Active compounds | Application rates (g of a.i./ha) | Winter wheat (5 days) | Winter wheat (20 days) | Winter barley (5 days) | Winter barley (21 days) | Winter barley (22 days) | Winter wheat (22 days) |
|---|---|---|---|---|---|---|---|
| (I-6) | 15 | 30 | 20 | 60 | 50 | — | — |
| (I-6) | 8 | 30 | 10 | 40 | 50 | 20 | 20 |
| (I-6) | 4 | 20 | 10 | 30 | 50 | 10 | 20 |
| (I-6) + cloquintocet-mexyl | 15 + 15 | 30 | 10 | 40 | 40 | — | — |
| (I-6) + cloquintocet-mexyl | 4 + 4 | 10 | 5 | 20 | 20 | 5 | 5 |
| (I-6) + cloquintocet-mexyl | 8 + 25 | — | — | — | — | 5 | 5 |
| (I-6) + fenchlor-azol-ethyl | 15 + 15 | 20 | 10 | 30 | 30 | — | — |
| (I-6) + fenchlor-azol-ethyl | 8 + 8 | 20 | 10 | 30 | 20 | 10 | — |
| (I-6) + fenchlor-azol-ethyl | 4 + 4 | 10 | 5 | 20 | 20 | — | — |
| (I-6) + fenchlor-azol-ethyl | 8 + 25 | | | | | 10 | — |

All variants were treated with 0.1% Renex-36 in the spray liquor.

Furthermore, in this test combinations of the compound (I-6) with the compound 2,2-dichloro-N,N-di-2-propenyl-acetamide (dichlormid) show considerably better compatibility with crop plants, such as, for example, barley and wheat, than the compound (I-6) on its own (cf Table A4).

TABLE A4

Post-emergence test in barley and wheat

| Active compounds | Application rates (g of a.i./ha) | Summer wheat (5 days) | Summer wheat (21 days) | Winter barley (5 days) |
|---|---|---|---|---|
| (I-6) | 30 | 50 | 40 | — |
| (I-6) | 15 | 40 | 30 | 50 |
| (I-6) + dichlormid | 30 + 30 | 30 | 20 | — |
| (I-6) + dichlormid | 15 + 15 | 20 | 20 | 30 |

All variants were treated with 0.1% Renex-36 in the spray liquor.

Furthermore, in this test combinations of the compound (I-6) with the compound 4,6-dichloro-2-phenyl-pyrimidine (fenclorim) show considerably better compatibility with crop plants, such as, for example, barley and wheat, than the compound (I-6) on its own (cf. Table A5).

TABLE A5

Post-emergence test in barley and wheat

| Active compounds | Application rates (g of a.i./ha) | Winter barley (5 days) | Winter barley (21 days) | Summer wheat (5 days) | Summer wheat (21 days) | Durum wheat (5 days) | Durum wheat (21 days) |
|---|---|---|---|---|---|---|---|
| (I-6) | 30 | 50 | 20 | 50 | 40 | 30 | 20 |
| (I-6) | 15 | 50 | 20 | 40 | 30 | 20 | 20 |

TABLE A5-continued

Post-emergence test in barley and wheat

| Active compounds | Application rates (g of a.i./ha) | Winter barley (5 days) | Winter barley (21 days) | Summer wheat (5 days) | Summer wheat (21 days) | Durum wheat (5 days) | Durum wheat (21 days) |
|---|---|---|---|---|---|---|---|
| (I-6) + fenclorim | 30 + 30 | 30 | 10 | 40 | 20 | 10 | 5 |
| (I-6) + fenclorim | 15 + 15 | 30 | 10 | 20 | 10 | 10 | 5 |

All variants were treated with 0.1% Renex-36 in the spray liquor.

Furthermore, in this test, combinations of the compound (I-6) with the compound 4-dichloroacetyl-3,4-dihydro-3-methyl-2H-1,4-benzoxazine (benoxacor) show considerably better compatibility with crop plants, such as, for example, barley and wheat, than the compound (I-6) on its own (cf. Table A6).

TABLE A6

Post-emergence test in barley and wheat

| Active compounds | Application rates (g of a.i./ha) | Summer wheat (5 days) | Summer wheat (21 days) | Durum wheat (21 days) | Winter barley (5 days) |
|---|---|---|---|---|---|
| (I-6) | 30 | 50 | 40 | 20 | — |
| (I-6) | 15 | 40 | 30 | 20 | 50 |
| (I-6) + benoxacor | 30 + 30 | 40 | 20 | 10 | — |
| (I-6) + benoxacor | 15 + 15 | 30 | 20 | 10 | 30 |

All variants were treated with 0.1% Renex-36 in the spray liquor.

Furthermore, in this test combinations of the compound (I-3) with the compounds 2,4-D and glyphosate-isopropylammonium show considerable synergistic activity (cf. Table A7).

TABLE A7

Post-emergence test (in brackets: values calculated according to Colby)

| Active compounds | Application rates g of a.i./ha | Amaranthus | Galium |
|---|---|---|---|
| (I-3) | 8 | — | 40 |
| (I-3) | 4 | 70 | — |
| 2,4-D | 86 | 30 | 0 |
| (I-3) + 2,4-D | 4 + 86 | 90 (79) | — |
| (I-3) + 2,4-D | 8 + 86 | — | 99 (40) |
| glyphosate-isopropylammonium | 125 | — | 0 |
| (I-3) + glyphosate-isopropylammonium | 8 + 125 | — | 80 (40) |

Furthermore, in this test, combinations of the compound (I-3) with the compound sulfentrazone show considerable synergistic activity (Table A8).

TABLE A8

Post-emergence test (in brackets: values calculated according to Colby)

| Active compounds | Application rates (g of a.i./ha) | Datura | Abutilon | Amaranthus | Chenopodium | Galium | Matricaria | Polygonum | Solanum | Veronica |
|---|---|---|---|---|---|---|---|---|---|---|
| (I-3) | 8 | 60 | — | — | — | 0 | — | 60 | — | 70 |
| (I-3) | 4 | 30 | 0 | 0 | 0 | — | 70 | — | 30 | 0 |
| sulfentrazone | 125 | 0 | — | — | — | — | 0 | 50 | 0 | 20 |
| sulfentrazone | 60 | 0 | 0 | 90 | 60 | 0 | — | — | 0 | 0 |
| (I-3) + sulfentrazone | 8 + 125 | 100 (60) | — | — | — | — | — | 100 (80) | — | 100 (76) |
| (I-3) + sulfentrazone | 4 + 125 | 100 (30) | — | — | — | — | 100 (70) | — | 100 (30) | 100 (20) |
| (I-3) + sulfentrazone | 8 + 60 | 100 (60) | — | — | — | 100 (0) | — | — | — | 100 (70) |
| (I-3) + sulfentrazone | 4 + 60 | 70 (30) | 98 (0) | 100 (90) | 100 (60) | — | — | — | 95 (30) | 100 (0) |

Furthermore, in this test combinations of the compound (I-3) with the compound imazamox show considerable synergistic activity (cf. Table A9).

TABLE A9

Post-emergence test (in brackets: values calculated according to Colby)

| Active compounds | Application rates (g of a.i./ha) | Veronica | Solanum |
|---|---|---|---|
| (I-3) | 8 | 70 | — |
| (I-3) | 4 | 0 | 30 |
| imazamox | 15 | — | 0 |
| imazamox | 8 | 0 | — |
| (I-3) + imazamox | 8 + 8 | 100 (70) | — |
| (I-3) + imazamox | 4 + 8 | 80 (0) | — |
| (I-3) + imazamox | 4 + 15 | — | 95 (30) |

Furthermore, in this test, combinations of the compound (I-3) with the compound acetochlor show considerable synergistic activity (cf. Table A10).

TABLE A10

Pre-emergence test (in brackets: values calculated according to Colby)

| Active compounds | Application rates (g of a.i./ha) | Alopecurus | Cyperus | Digitaria | Echinochloa | Setaria | Abutilon | Matricaria | Polygonum | Stellaria |
|---|---|---|---|---|---|---|---|---|---|---|
| (I-3) | 8 | 0 | — | 20 | — | — | 50 | — | 90 | — |
| (I-3) | 4 | — | 0 | 0 | 0 | 0 | 20 | 50 | 0 | 80 |
| acetochlor | 250 | — | 60 | — | 80 | 80 | 40 | — | 30 | — |
| acetochlor | 125 | 30 | 60 | 80 | — | — | 0 | 90 | 30 | 80 |
| (1-3) + acetochlor | 8 + 125 | 80 (30) | — | 100 (84) | — | — | 100 (50) | — | — | — |
| (I-3) + acetochlor | 4 + 125 | — | 90 (60) | 90 (80) | — | — | 100 (20) | 100 (95) | 80 (30) | 100 (96) |
| (I-3) + acetochlor | 8 + 250 | — | — | — | — | — | 100 (70) | — | 100 (93) | — |
| (I-3) + acetochlor | 4 + 250 | — | 99 (60) | — | 95 (80) | 99 (80) | — | — | 100 (30) | — |

Furthermore, in this test combinations of the compound (I-3) with the compound metolachlor show considerable synergistic activity (cf. Table A11).

TABLE A11

Pre-emergence test (in brackets: values calculated according to Colby)

| Active compounds | Application rates (g of a.i./ha) | Digitaria | Abutilon | Stellaria | Ipomoea | Viola |
|---|---|---|---|---|---|---|
| (I-3) | 8 | 20 | 50 | — | — | 90 |
| (I-3) | 4 | — | 20 | 80 | 30 | — |
| metolachlor | 250 | 90 | 30 | 80 | 30 | — |
| metolachlor | 125 | — | 30 | 30 | — | 50 |
| (I-3) + metolachlor | 8 + 250 | 100 (92) | 100 (65) | — | — | — |
| (I-3) + metolachlor | 8 + 125 | — | 100 (65) | — | 100 (51) | 100 (95) |
| (I-3) + metolachlor | 4 + 125 | — | 100 (44) | 100 (86) | — | — |

Furthermore, in this test combinations of the compound (I-3) with the compound isoxaflutole show considerable synergistic activity (cf. Table A12).

TABLE A12

Pre-emergence test (in brackets: values calculated according to Colby)

| Active compounds | Application rates (g of a.i./ha) | Alopecurus | Digitaria | Polygonum | Abutilon | Datura |
|---|---|---|---|---|---|---|
| (I-3) | 8 | 0 | 20 | 90 | 40 | 30 |
| (I-3) | 4 | — | 0 | — | 20 | — |
| Isoxaflutole | 60 | 40 | — | — | — | 90 |
| Isoxaflutole | 30 | — | 90 | 0 | 80 | — |
| (I-3) + Isoxaflutole | 8 + 60 | 80 (40) | — | — | — | 100 (93) |
| (I-3) + isoxaflutole | 8 + 30 | — | 99 (92) | 100 (90) | 100 (88) | — |
| (I-3) + isoxaflutole | 4 + 30 | — | 99 (90) | — | 100 (84) | — |

Furthermore, in this test combinations of the compound (I-3) with the compound flufenacet show considerable synergistic activity (cf. Table A13).

TABLE A13

Pre-emergence test (in brackets: values calculated according to Colby)

| Active compounds | Application rates (g of a.i./ha) | Digitaria | Setaria | Abutilon | Datura | Ipomoea | Matricaria | Stellaria |
|---|---|---|---|---|---|---|---|---|
| (I-3) | 8 | 20 | 0 | 50 | 80 | — | 90 | — |
| (I-3) | 4 | — | 0 | 20 | — | 50 | 50 | 80 |
| flufenacet | 125 | — | — | 20 | — | 30 | 60 | 70 |
| flufenacet | 60 | 80 | 80 | 20 | 40 | — | — | 50 |
| (I-3) + flufenacet | 8 + 125 | — | — | 100 (60) | — | — | 100 (96) | — |
| (I-3) + flufenacet | 8 + 60 | 100 (84) | 100 (80) | 100 (60) | 99 (88) | — | — | — |
| (I-3) + flufenacet | 4 + 125 | — | — | 100 (36) | — | 99 (65) | 100 (80) | 100 (94) |
| (I-3) + flufenacet | 4 + 60 | — | 100 (80) | 95 (36) | — | — | — | 100 (90) |

Furthermore, in this test combinations of the compound (I-3) with the compound metribuzin show considerable synergistic activity (cf. Table A14).

TABLE A14

Pre-emergence test (in brackets: values calculated according to Colby)

| Active compounds | Application rates (g of a.i./ha) | Abutilon | Datura | Echinochloa | Chenopodium |
|---|---|---|---|---|---|
| (I-3) | 8 | 50 | 80 | — | — |
| (I-3) | 4 | 20 | — | 0 | 80 |
| metribuzin | 125 | — | — | 80 | — |
| metribuzin | 60 | 90 | 30 | — | 50 |
| (I-3) + metribuzin | 4 + 125 | — | — | 95 (80) | — |
| (I-3) + metribuzin | 8 + 60 | 100 (95) | 100 (86) | — | — |
| (I-3) + metribuzin | 4 + 60 | 100 (92) | — | — | 100 (96) |

Furthermore, in this test combinations of the compound (I-3) with the compound amicarbazone show considerable synergistic activity (cf. Table A15).

TABLE A15

Pre-emergence test (in brackets: values calculated according to Colby)

| Active compounds | Application rates (g of a.i./ha) | Alopecurus | Digitaria | Echinochloa | Eriochloa | Setaria | Datura |
|---|---|---|---|---|---|---|---|
| (I-3) | 8 | 0 | 20 | 0 | 50 | 0 | 80 |
| (I-3) | 4 | 0 | — | — | 30 | 0 | — |
| amicarbazone | 60 | 20 | 60 | 0 | 70 | 20 | 20 |
| (I-3) + amicarbazone | 8 + 60 | 80 (20) | 100 (68) | 90 (0) | 95 (85) | 100 (20) | 99 (84) |
| (I-3) + amicarbazone | 4 + 60 | 80 (20) | — | — | 95 (79) | 100 (20) | — |

Furthermore, in this test combinations of the compound (I-3) with the compound sulcotrione show considerable synergistic activity (cf. Table A16).

TABLE A16

Pre-emergence test (in brackets: values calculated according to Colby)

| Active compounds | Application rates (g of a.i./ha) | Abutilon | Stellaria | Matricaria | Cyperus | Datura | Ipomoea |
|---|---|---|---|---|---|---|---|
| (I-3) | 8 | 50 | — | 90 | 30 | 30 | 30 |
| (I-3) | 4 | 20 | 80 | 50 | — | — | — |
| sulcotrione | 60 | 80 | 80 | — | — | — | 80 |
| sulcotrione | 30 | 70 | — | 40 | 90 | 50 | — |
| (I-3) + sulcotrione | 8 + 60 | 100 (90) | — | — | — | — | 100 (86) |
| (I-3) + sulcotrione | 4 + 60 | 100 (84) | 100 (96) | — | — | — | — |
| (I-3) + sulcotrione | 8 + 30 | 100 (85) | — | 100 (94) | 100 (93) | 100 (65) | — |
| (I-3) + sulcotrione | 4 + 30 | 100 (76) | — | 99 (70) | — | — | — |

Furthermore, in this test combinations of the compound (I-3) with the compounds flufenacet and amicarbazone show considerable synergistic activity (cf. Table A17).

TABLE A17

Pre-emergence test (in brackets: values calculated according to Colby)

| Active compounds | Application rates (g of a.i./ha) | Digitaria | Eriochloa | Abutilon | Cassia | Datura | Ipomoea | Setaria | Chenopodium |
|---|---|---|---|---|---|---|---|---|---|
| (I-3) | 8 | 20 | — | 50 | — | 80 | — | 0 | — |
| (I-3) | 4 | 0 | 30 | 20 | 40 | 30 | 50 | 0 | 80 |
| flufenacet | 60 | 80 | — | 20 | 60 | 40 | 30 | 90 | 50 |
| flufenacet | 30 | 80 | 80 | 20 | — | 20 | 30 | 70 | 30 |
| amicarbazone | 60 | 60 | — | 99 | — | 20 | — | 30 | — |
| amicarbazone | 30 | 20 | 30 | 20 | 70 | 0 | 50 | 20 | 50 |
| (I-3) + flufenacet + amicarbazone | 8 + 60 + 30 | 99 (87) | — | 100 (68) | — | 100 (88) | — | 100 (92) | — |
| (I-3) + flufenacet + amicarbazone | 8 + 30 + 30 | 99 (87) | — | 100 (68) | — | 100 (84) | — | 100 (76) | — |
| (I-3) + flufenacet + amicarbazone | 4 + 30 + 30 | — | 100 (90) | 100 (49) | — | — | 99 (83) | 100 (76) | 100 (93) |
| (I-3) + flufenacet + amicarbazone | 4 + 60 + 30 | — | — | 100 (49) | 100 (93) | 100 (58) | 99 (83) | 100 (92) | 100 (95) |

Furthermore, in this test combinations of the compound (I-3) with the compounds flufenacet and metribuzin show considerable synergistic activity (cf. Table A18).

TABLE A18

Pre-emergence test (in brackets: values calculated according to Colby)

| Active compounds | Application rates (g of a.i./ha) | Alopecurus | Bromus | Digitaria | Echinochloa | Abutilon | Datura | Galium | Ipomoea | Polygonum |
|---|---|---|---|---|---|---|---|---|---|---|
| (I-3) | 8 | — | — | 20 | 0 | 50 | 80 | 30 | — | — |
| (I-3) | 4 | 0 | 0 | 0 | — | 20 | — | — | 50 | 0 |
| flufenacet | 60 | 70 | 30 | 80 | 90 | 20 | 40 | — | 30 | 30 |
| flufenacet | 30 | — | — | 80 | — | 20 | 20 | 30 | — | — |
| metribuzin | 60 | — | — | 80 | 0 | 90 | 30 | 0 | — | 40 |

TABLE A18-continued

Pre-emergence test (in brackets: values calculated according to Colby)

| Active compounds | Application rates (g of a.i./ha) | Alopecurus | Bromus | Digitaria | Echinochloa | Abutilon | Datura | Galium | Ipomoea | Polygonum |
|---|---|---|---|---|---|---|---|---|---|---|
| metribuzin | 30 | 0 | 0 | 30 | — | 80 | 20 | — | 0 | — |
| (I-3) + flufenacet + metribuzin | 8 + 60 + 60 | — | — | — | 100 (90) | 100 (96) | 100 (92) | — | — | — |
| (I-3) + flufenacet + metribuzin | 8 + 30 + 60 | — | — | — | — | 100 (96) | 100 (89) | 100 (51) | — | — |
| (I-3) + flufenacet + metribuzin | 4 + 60 + 60 | — | — | 100 (96) | — | 100 (94) | — | — | — | 90 (58) |
| (I-3) + flufenacet + metribuzin | 4 + 60 + 30 | 90 (70) | 80 (30) | 100 (86) | — | 100 (87) | — | — | 100 (65) | — |
| (I-3) + flufenacet + metribuzin | 4 + 30 + 60 | — | — | 100 (96) | — | 100 (94) | — | — | — | — |
| (I-3) + flufenacet + metribuzin | 8 + 30 + 30 | — | — | — | — | 100 (92) | 100 (87) | — | — | — |

Furthermore, in this test combinations of the compound (I-3) with the compounds flufenacet and amicarbazone show considerable synergistic activity (cf Table A19).

TABLE A19

Pre-emergence test (in brackets: values calculated according to Colby)

| Active compounds | Application rates (g of a.i./ha) | Lolium | Polygonum |
|---|---|---|---|
| (I-3) | 8 | 20 | — |
| (I-3) | 4 | — | 0 |
| flufenacet | 60 | 80 | — |
| flufenacet | 30 | — | 20 |
| amicarbazone | 60 | — | 80 |
| amicarbazone | 30 | 0 | — |
| (I-3) + flufenacet + amicarbazone | 8 +60 +30 | 100 (84) | — |
| (I-3) + flufenacet + amicarbazone | 4 +30 +60 | — | 99 (84) |

Furthermore, in this test combinations of the compound (I-3) with the compound acetochlor show considerable synergistic activity (cf. Table A20).

TABLE A20

Pre-emergence test (in brackets: values calculated according to Colby)

| Active compounds | Application rates (g of a.i./ha) | Lolium | Chenopodium | Datura | Galium | Ipomoea |
|---|---|---|---|---|---|---|
| (I-3) | 8 | — | — | 30 | 20 | 30 |
| (I-3) | 4 | 0 | 80 | 0 | — | 30 |
| acetochlor | 250 | 90 | — | 50 | 20 | 20 |
| acetochlor | 125 | — | 30 | 30 | 0 | 0 |
| (I-3) + acetochlor | 8 + 250 | — | — | 100 (65) | 95 (36) | 100 (44) |
| (I-3) + acetochlor | 8 + 125 | — | — | 99 (51) | 80 (20) | 100 (30) |
| (I-3) + acetochlor | 4 + 250 | 100 (90) | — | 100 (50) | — | 95 (44) |
| (I-3) + acetochlor | 4 + 125 | — | 90 (86) | 95 (30) | — | 95 (30) |

Furthermore, in this test combinations of the compound (I-3) with the compound flufenacet show considerable synergistic activity (cf. Table A21).

TABLE A21

Pre-emergence test (in brackets: values calculated according to Colby)

| Active compounds | Application rates (g of a.i./ha) | Chenopodium | Datura | Ipomoea | Polygonum |
|---|---|---|---|---|---|
| (I-3) | 8 | — | — | 30 | 90 |
| (I-3) | 4 | 80 | 0 | — | 40 |
| Flufenacet | 125 | — | 50 | 80 | 30 |
| flufenacet | 60 | 50 | — | 70 | 0 |
| (I-3) + flufenacet | 8 + 125 | — | — | 100 (86) | 100 (93) |
| (I-3) + flufenacet | 4 + 125 | — | 99 (50) | — | 100 (58) |

TABLE A21-continued

Pre-emergence test (in brackets: values calculated according to Colby)

| Active compounds | Application rates (g of a.i./ha) | Cheno-podium | Datura | Ipomoea | Polygonum |
|---|---|---|---|---|---|
| (I-3) + flufenacet | 8 + 60 | — | — | 95 (79) | 100 (90) |
| (I-3) + flufenacet | 4 + 60 | 100 (90) | — | — | — |

Furthermore, in this test combinations of the compound (I-3) with the compound amicarbazone show considerable synergistic activity (cf. Table A22).

TABLE A22

Pre-emergence test (in brackets: values calculated according to Colby)

| Active compounds | Application rates (g of a.i./ha) | Cassia | Datura | Polygonum |
|---|---|---|---|---|
| (I-3) | 8 | 50 | — | — |
| (I-3) | 4 | — | 0 | 40 |
| amicarbazone | 125 | — | 50 | 90 |
| amicarbazone | 60 | 80 | — | — |
| (I-3) + amicarbazone | 8 + 60 | 100 (90) | — | — |
| (I-3) + amicarbazone | 4 + 125 | — | 90 (50) | 99 (94) |

Furthermore, in this test combinations of the compound (I-3) with the compounds flufenacet and metribuzin show considerable synergistic activity (cf. Table A23).

TABLE 23

Pre-emergence test (in brackets: values calculated according to Colby)

| Active compounds | Application rates (g of a.i./ha) | Eriochloa | Lolium | Setaria | Chenopodium | Galium | Ipomoea |
|---|---|---|---|---|---|---|---|
| (I-3) | 8 | 50 | — | 0 | — | — | 30 |
| (I-3) | 4 | — | 0 | 0 | 80 | 0 | — |
| flufenacet | 60 | 90 | — | 90 | 50 | 40 | — |
| flufenacet | 30 | — | 70 | 70 | 30 | — | 50 |
| metribuzin | 60 | 0 | — | 80 | — | 20 | 0 |
| metribuzin | 30 | — | 0 | 20 | 30 | — | — |
| (I-3) + flufenacet + metribuzin | 8 + 60 + 60 | 100 (95) | — | — | — | — | — |
| (I-3) + flufenacet + metribuzin | 8 + 30 + 60 | — | — | 100 (94) | — | — | 90 (65) |
| (I-3) + flufenacet + metribuzin | 4 + 60 + 60 | — | — | — | — | 95 (52) | — |
| (I-3) + flufenacet + metribuzin | 4 + 60 + 30 | — | — | — | 100 (93) | — | — |
| (I-3) + flufenacet + metribuzin | 4 + 30 + 60 | — | 95 (70) | — | — | — | — |
| (I-3) + flufenacet + metribuzin | 8 + 30 + 30 | — | — | 100 (76) | — | — | — |

Furthermore, in this test combinations of the compound (I-3) with the compound trifluralin show considerable synergistic activity (cf. Table A24).

TABLE A24

Pre-emergence test (in brackets: values calculated according to Colby)

| Active compounds | Application rates (g of a.i./ha) | Echino-chloa | Setaria | Lolium | Cassia | Veronica |
|---|---|---|---|---|---|---|
| (I-3) | 8 | 30 | 30 | — | — | — |
| (I-3) | 4 | 30 | — | 0 | 0 | 30 |
| trifluralin | 500 | 95 | — | — | — | 95 |
| trifluralin | 250 | — | 95 | 95 | 80 | — |
| (I-3) + trifluralin | 8 + 500 | 99 (96) | — | — | — | — |
| (I-3) + trifluralin | 4 + 500 | 100 (96) | — | — | — | 100 (96) |
| (I-3) + trifluralin | 8 + 250 | — | 100 (96) | — | — | — |
| (I-3) + trifluralin | 4 + 250 | — | — | 100 (95) | 100 (80) | — |

Furthermore, in this test combinations of the compound (I-3) with the compound atrazine show considerable synergistic activity (cf. Table A25).

TABLE A25

Pre-emergence test (in brackets: values calculated according to Colby)

| Active compounds | Application rates (g of a.i./ha) | Avena | Bromus | Cyperus | Lolium |
|---|---|---|---|---|---|
| (I-3) | 8 | 40 | — | 50 | 60 |
| (I-3) | 4 | — | 0 | — | — |
| atrazine | 500 | 80 | 70 | 50 | 90 |
| (I-3) + atrazine | 8 + 500 | 100 (88) | | 100 (75) | 100 (96) |
| (I-3) + atrazine | 4 + 500 | — | 100 (70) | — | — |

Furthermore, in this test combinations of the compound (I-3) with the compounds isoxaflutole and metribuzin show considerable synergistic activity (cf. Table A26).

TABLE A26

Pre-emergence test (in brackets: values calculated according to Colby)

| Active compounds | Application rates (g of a.i./ha) | Avena | Digitaria | Echinochloa | Lolium | Setaria | Cassia | Matricaria |
|---|---|---|---|---|---|---|---|---|
| (I-3) | 8 | — | — | 30 | 30 | 30 | 30 | 70 |
| (I-3) | 4 | 40 | 30 | 0 | 30 | 0 | — | 30 |
| isoxaflutole | 60 | — | — | 40 | 50 | 30 | — | 40 |
| isoxaflutole | 30 | 30 | 80 | 30 | 30 | 30 | 70 | 20 |
| metribuzin | 125 | 40 | 90 | 80 | 70 | 80 | — | 70 |
| metribuzin | 60 | — | — | 30 | — | — | 80 | 60 |
| (I-3) + isoxaflutole + metribuzin | 8 + 60 + 125 | — | — | — | 100 (89) | 100 (90) | — | 99 (95) |
| (I-3) + isoxaflutole + metribuzin | 4 + 60 + 125 | — | — | — | 100 (88) | — | — | 99 (87) |
| (I-3) + isoxaflutole + metribuzin | 8 + 30 + 60 | — | — | — | — | — | 100 (96) | 99 (90) |
| (I-3) + isoxaflutole + metribuzin | 4 + 30 + 125 | 99 (75) | 100 (98) | 100 (86) | 100 (85) | 100 (86) | — | 95 (83) |
| (I-3) + isoxaflutole + metribuzin | 8 + 60 + 60 | — | — | 100 (71) | — | — | — | 99 (93) |

Furthermore, in this test combinations of the compound (I-3) with the compound foramsulfuron show considerable synergistic activity (cf. Table A27).

TABLE A27

Pre-emergence test (in brackets: values calculated according to Colby)

| Active compounds | Application rates (g of a.i./ha) | Abutilon | Cassia | Polygonum |
|---|---|---|---|---|
| (I-3) | 8 | 95 | 30 | 20 |
| foramsulfuron | 30 | 50 | — | 40 |
| foramsulfuron | 15 | — | 50 | — |
| (I-3) + foramsulfuron | 8 + 30 | 100 (97) | — | 99 (52) |
| (I-3) + foramsulfuron | 8 + 15 | — | 99 (65) | — |

In this test, it is furthermore possible to demonstrate that in particular compounds of Group 3 are capable of antagonizing the damaging effect of active compounds of the formula (I) in crop plants. (Tab. A28–A32).

TABLE A28

Pre-emergence test in maize

| Active compounds | Application rates (g of a.i./ha) | Maize (7 days) | Maize (12 days) | Maize (21 days) |
|---|---|---|---|---|
| (I-3) | 90 | 20 | — | 36 |
| (I-3) | 60 | 10 | 20 | 17 |
| (I-3) + flurazole | 90 + 500 | 10 | — | 18 |
| (I-3) + flurazole | 60 + 500 | 5 | 5 | 8 |
| (I-3) + flurazole | 90 + 60 | — | — | 27 |

TABLE A29

Pre-emergence test in maize

| Active compounds | Application rates (g of a.i./ha) | Maize (12 days) | Maize (21 days) |
|---|---|---|---|
| (I-3) | 90 | 30 | 36 |
| (I-3) | 60 | 20 | — |
| (I-3) + AD-67 | 90 + 500 | 15 | 21 |
| (I-3) + AD-67 | 60 + 500 | 5 | — |
| (I-3) + AD-67 | 90 + 60 | 20 | 20 |
| (I-3) + AD-67 | 60 + 60 | 5 | — |
| (I-3) + AD-67 | 90 + 30 | — | 21 |

TABLE A30

Pre-emergence test in maize

| Active compounds | Application rates (g of a.i./ha) | Maize (7 days) | Maize (12 days) | Maize (21 days) |
|---|---|---|---|---|
| (I-6) | 90 | 60 | 60 | 30 |
| (I-6) | 60 | 30 | — | — |
| (I-6) + AD-67 | 90 + 500 | 30 | 40 | 19 |
| (I-6) + AD-67 | 90 + 60 | 20 | 20 | 24 |
| (I-6) + AD-67 | 90 + 30 | 20 | 30 | — |
| (I-6) + AD-67 | 60 + 30 | 10 | — | — |

TABLE A31

Pre-emergence test in maize

| Active compounds | Application rates (g of a.i./ha) | Maize (7 days) | Maize (12 days) | Maize (21 days) |
|---|---|---|---|---|
| (I-3) | 90 | 20 | 30 | 29 |
| (I-3) + AD-67 | 90 + 500 | 5 | 5 | 8 |
| (I-3) + AD-67 | 90 + 60 | 5 | 5 | 11 |
| (I-3) + AD-67 | 90 + 30 | — | 10 | 16 |

TABLE A32

Pre-emergence test in maize

| Active compounds | Application rates (g of a.i./ha) | Maize (7 days) | Maize (12 days) | Maize (21 days) |
|---|---|---|---|---|
| (I-5) | 90 | 60 | 70 | 64 |
| (I-5) | 60 | 20 | 30 | 18 |
| (I-5) + AD-67 | 90 + 500 | 10 | 5 | 20 |
| (I-5) + AD-67 | 60 + 500 | — | 10 | 6 |
| (I-5) + AD-67 | 90 + 60 | 30 | 30 | 16 |
| (I-5) + AD-67 | 60 + 60 | 5 | 10 | 9 |
| (I-5) + AD-67 | 60 + 30 | — | 10 | 8 |

What is claimed is:

1. A herbicidal composition comprising a synergistically effective amount of (a) at least one N-aryl-uracil of the formula (I)

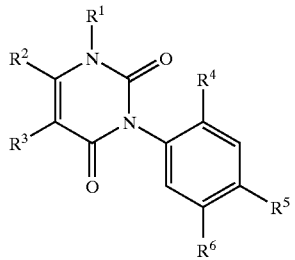

(I)

wherein
R$^1$ represents amino or methyl,
R$^2$ represents trifluoromethyl,
R$^3$ represents hydrogen, chlorine or methyl,
R$^4$ represents hydrogen, fluorine, or chlorine,
R$^5$ represents cyano, thiocarbamoyl, or chlorine, and
R$^6$ represents carboxyl, carbamoyl, thiocarbamoyl, hydroxyl, mercapto, amino, fluorine, chlorine, or bromine, represents optionally cyano-, carboxyl-, hydroxyl-, methoxy-, ethoxy-, acetyl-, propionyl-, methoxycarbonyl-, ethoxycarbonyl-, n- or i-propoxycarbonyl-, allyloxycarbonyl-, and/or propargyloxy-carbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, represents optionally cyano-, carboxyl-, fluorine-, chlorine-, bromine-, and/or methoxycarbonyl- and/or ethoxycarbonyl-substituted ethenyl, propenyl, ethynyl, propynyl, propenyloxy, or propynyloxy, or represents N-(2,2-dimethyl-propanoyl)-N-ethylsulphonyl-amino or N-(2-methylpropanoyl)-N-ethylsulphonyl-amino, and (b) the herbicide 2-(2-chloro-4-methylsulphonyl-benzoyl)-cyclohexane-1,3-dione (sulcotrione).

2. The herbicidal composition of claim 1, wherein the at least one N-aryl uracil of formula (I) is selected from 1,1-dimethyl-2-oxo-2-(2-propenyloxy)-ethyl 2-chloro-5-(3, 6-dihydro-3-methyl-2,6-dioxo-4-trifluoromethyl-1(2H)-pyrimidinyl)-benzoate, 5-fluoro-4-(3-methyl-2,6-dioxo-4-trifluoromethyl-3,6-dihydro-1(2H)-pyrimidinyl)-2-[(1-methyl-2-propynyl)-oxy]-benzonitrile, N-[2-cyano-4-fluoro-5-(3-methyl-2,6-dioxo-4-trifluoromethyl-3,6-dihydro-1(2H)-pyrimidinyl)-phenyl]-N-(2,2-dimethyl-propanoyl)-1-ethanesulphonamide, N-[2-cyano-4-fluoro-5-(3-methyl-2,6-dioxo-4-trifluoromethyl-3,6-dihydro-1(2H)-pyrimidinyl)-phenyl]-N-(4-methoxy-benzoyl)-ethanesulfonamide, N-[5-(3-amino-2,6-dioxo-4-trifluoromethyl-3,6-dihydro-1(2H)-pyrimidinyl)-2-cyano-4-fluoro-phenyl]-N-(2-thienyl-carbonyl)-1-ethanesulphonamide, 2-(ethylsulphonylamino)-5-fluoro-4-[3-methyl-2,6-dioxo-4-trifluoromethyl-3,6-dihydro-1(2H)-pyrimidinyl]-benzenecarbothioamide.

3. A herbicidal composition according to claim 1 additionally comprising (c) a compound that improves crop plant compatibility selected from the group consisting of 4-dichloroacetyl-1-oxa-4-aza-spiro[4.5]-decane (AD-67), 1-dichloroacetyl-hexahydro-3,3,8a-trimethylpyrrolo[1, 2-a]-pyrimidin-6(2H)-one (BAS-145138), 4-dichloroacetyl-3,4-dihydro-3-methyl-2H-1,4-benzoxazine (benoxacor), 1-methyl-hexyl 5-chloro-quinoxalin-8-oxy-acetate (cloquintocetmexyl), α-(cyanomethoximino)-phenylacetonitrile (cyometrinil), 2,4-dichlorophenoxy-acetic acid (2,4-D), 2,2-dichloro-N-(2-oxo-2-(2-propenylamino)-ethyl)-N-(2-propenyl)-acetamide (DKA-24), 2,2-dichloro-N,N-di-2-propenylacetamide (dichlormid), N-(4-methyl-phenyl)-N'-(1-methyl-1-phenyl-ethyl)-urea (dymron), 4,6-dichloro-2-phenyl-pyrimidine (fenclorim), ethyl 1-(2,4-dichlorophenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), (4-chloro-2-methyl-phenoxy)-acetic acid (MCPA), (+-)-2-(4- chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2,5-trimethyl-oxazolidine (R-29148), N-cyclopropyl4-[[(2-methoxy-5-methyl-benzoyl)-amino]-sulphonyl]-benzamide, N-[(4-methoxy-acetylamino)-phenyl]-sulphonyl-2-methoxy-benzamide and N-[(4-methylaminocarbonylamino)-phenyl]-sulphonyl-2-methoxy-benzamide.

4. The herbicidal composition of claim 1, additionally comprising a compound which improves plant compatibility comprising at least one of 1-methyl-hexyl 5-chloro-quinoxalin-8-oxy-acetate (cloquintocet-mexyl), ethyl 4,5-dihydro-5,5-diphenyl-3-isoxazole-carboxylate (isoxadifen-ethyl), diethyl 1-(2,4-dichloro-phenyl)-4,5-dihydro-5-methyl-1H-pyrazole-3,5-dicarboxylate (mefenpyr-diethyl), 4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 2,2-dichloro-N,N-di-2-propenyl-acetamide (dichlormid), 3-dichloroacetyl-5-(2-furanyl)-2,2-dimethyl-oxazolidine (furilazole, MON-13900) and 3-dichloroacetyl-2,2,5-trimethyl-oxazolidine (R-29148).

5. A method for controlling plant growth comprising applying a synergistically effective amount of the composition of claim 1 to at least one of the plant and/or its habitat.

6. A process for preparing a herbicidal composition comprising mixing a synergistically effective amount of the composition of claim 1 with at least one of surfactants and extenders.

* * * * *